US006608717B1

(12) United States Patent
Medford et al.

(10) Patent No.: US 6,608,717 B1
(45) Date of Patent: Aug. 19, 2003

(54) OPTICAL COHERENCE MICROSCOPE AND METHODS OF USE FOR RAPID IN VIVO THREE-DIMENSIONAL VISUALIZATION OF BIOLOGICAL FUNCTION

(75) Inventors: June I. Medford, Fort Collins, CO (US); Richard C. Haskell, Claremont, CA (US); Barbara M. Hoeling, San Dimas, CA (US); Daniel C. Petersen, Claremont, CA (US); Ruye Wang, Claremont, CA (US); Mary E. Williams, Claremont, CA (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/493,896

(22) Filed: Jan. 28, 2000

Related U.S. Application Data

(60) Provisional application No. 60/117,963, filed on Jan. 29, 1999.

(51) Int. Cl.$^7$ .............................................. G02B 21/00
(52) U.S. Cl. ...................................... 359/368; 356/479
(58) Field of Search ........................ 356/479; 359/368, 359/376

(56) References Cited

U.S. PATENT DOCUMENTS

| 5,321,501 A | 6/1994 | Swanson et al. ............ 356/479 |
| 5,459,570 A | 10/1995 | Swanson et al. ............ 356/479 |
| 5,570,182 A | * 10/1996 | Nathel et al. ................ 356/479 |

OTHER PUBLICATIONS

Hee et al., "Micron–resolution Optical Coherence Tomography of the Human Eye," *Advances in Optical Imaging and Photon Migration*, pp. 235–238, 1994.

Izatt et al., "Optical Coherence Microscopy," *Advances in Optical Imaging and Photon Migration*, pp. 249–252, 1994.

Barnoski et al., "Fiber waveguides: a novel technique for investigating attenuation characteristics," *Applied Optics*, 15:2112–2115 (1976).

Bouma et al., "High–resolution optical coherence tomographic imaging using a mode–locked Ti:Al$_2$O$_3$ laser source," *Optics Letters*, 20:1486–1488 (1995).

Clivaz et al., "High–resolution reflectometry in biological tissues," *Optics Letters*, 17:4–6 (1992).

Danielson et al., "Guided–wave reflectometry with micrometer resolution," *Applied Optics*, 26:2836–2842 (1987).

Fercher et al., "Eye–length measurement by interferometry with partially coherent light," *Optics Letters*, 13:186–188 (1988).

Flock et al., "Optical Properties of Intralipid: A Phantom Medium for Light Propagation Studies," *Lasers in Surgery and Medicine*, 12:510–519 (1992).

Flock et al., "Total attenuation coefficients and scattering phase functions of tissues and phantom materials at 633 nm," *Med. Phys.*, 14:835–841 (1987).

Hee et al., "Polarization–sensitive low–coherence reflectometer for birefringence characterization and ranging," *J. Opt. Soc. Amer. B*, 9:903–908 (1992).

(List continued on next page.)

*Primary Examiner*—Euncha Cherry
(74) *Attorney, Agent, or Firm*—Knobbe, Martens, Olson & Bear, LLP

(57) ABSTRACT

A high resolution optical coherence microscope system for visualizing structures below a surface of a biological sample is provided. The system includes a light source emitting light in a wavelength of between 700 and 1500 nm, the light being directed along a sample path and a reference path. The length of at least one of the paths is a modulated path having a selected amplitude of modulation that is equal to or less than about 3 fringes of the wavelength.

23 Claims, 10 Drawing Sheets

OTHER PUBLICATIONS

Hitzenberger, "Optical Measurement of the Axial Eye Length by Laser Doppler Interferometry," *Investigative Ophthalmology & Visual Science*, 32:616–624 (1991).

Huang et al., "Micron–Resolution Ranging of Cornea Anterior Chamber by Optical Reflectometry," *Lasers in Surgery and Medicine*, 11:419–425 (1991).

Izatt et al., "Optical coherence microscopy in scattering media," *Optics Letters*, 19:590–592 (1994).

Jacobs et al., "Magnetic Resonance Microscopy of Embryonic Cell Lineages and Movements," *Science*, 263:681–684 (1994).

Knüttel et al., "Low–coherence reflectometry for stationary lateral and depth profiling with acousto–optic deflectors and a CCD camera," *Optics Letters*, 19:302–304 (1994).

Knüttel et al., "Stationary depth–profiling reflectometer based on low–coherence interferometry," *Optics Communications*, 102:193–198 (1993).

Kobayashi et al., "Polarization–Independent Interferometric Optical–Time–Domain Reflectometer," *IEEE Journal of Lightwave Technology*, 9:623–628 (1991).

O'Rourke et al., "Rapid Remodeling of Retinal Arbors in the Tectum with and without Blockade of Synaptic Transmission," *Neuron*, 12:921–934 (1994).

Potter et al., "Intravital imaging of green fluorescent protein using two–photon laser–scanning microscopy," *Gene* 173:25–31 (1996).

Schmitt et al., "Low Coherence Interferometry for Imaging Microstructures within Optically Turbid Tissues," *Advances in Optical Imaging and Photon Migration*, pp. 253–256 (1994).

Schmitt et al., "Measurement of optical properties of biological tissues by low–coherence reflectometry," *Applied Optics*, 32:6032–6042 (1993).

Schmitt et al., "Confocal microscopy in turbid media," *J. Opt. Soc. Am.*, 11:2226–2235 (1994).

Schmitt et al., "Optical–coherence tomography of a dense tissue: statistics of attenuation and backscattering," *Phys. Med. Biol.*, 39:1705–1720 (1994).

Schmitt et al., "Subsurface Imaging of Living Skin with Optical Coherence Microscopy," *Dermatology*, 191:93–98 (1995).

Sorin et al., "A Simple Intensity Noise Reduction Technique for Optical Low–Coherence Reflectometry," *IEEE Photonics Technology Letters*, 4:1404–1406 (1992).

Swanson et al., "High–speed optical coherence domain reflectometry," *Optics Letters*, 17:151–153 (1992).

Swanson et al., "In vivo retinal imaging by optical coherence tomography," *Optics Letters*, 18:1864–1866 (1993).

Takada et al., "New measurement system for fault location in optical waveguide devices based on an interferometric technique," *Applied Optics*, 26:1603–1606 (1987).

Van Staveren et al., "Light scattering in Intralipid–10% in the wavelength range of 400–1100 nm," *Applied Optics*, 30:4507–4514 (1991).

Wang et al., "Characterization of human scalp hairs by optical low–coherence reflectometry," *Optics Letters*, 20:524–526 (1995).

Wilson et al., "Cell rearrangement and segmentation in Xenopus: direct observation of cultured explants," *Development*, 105:155–166 (1989).

Yadlowsky et al., "Multiple scattering in optical coherence microscopy," *Applied Optics*, 34:5699–5707 (1995).

Youngquist et al., "Optical coherence–domain reflectometry: a new optical evaluation technique," *Optics Letters*, 12:158–160 (1987).

* cited by examiner

Impedance of mounted and unmounted piezo versus driving voltage frequency.

Displacement of the mounted piezo per volt applied at the resonance frequencies.

Phase dependence of the output fringe signal.

OPTICAL COHERENCE MICROSCOPE AND METHODS OF USE FOR RAPID IN VIVO THREE-DIMENSIONAL VISUALIZATION OF BIOLOGICAL FUNCTION

RELATED APPLICATION

This application claims priority from United States Provisional Application No. 60/117,963, entitled OPTICAL COHERENCE MICROSCOPE AND METHODS OF USE FOR RAPID IN VIVO THREE-DIMENSIONAL VISUALIZATION OF BIOLOGICAL FUNCTION, filed on Jan. 29, 1999, which is hereby incorporated by reference.

This invention was made, in part, with government support under NSF Grant No. DBI-9612240 and NSF Grant No. DBI-0137973 awarded by the National Science Foundation. The Government may have certain rights in this invention.

BACKGROUND OF THE INVENTION

1. Field of the Invention

The present invention relates to an optical coherence microscope (OCM) for study of problems in developmental biology and biotechnology. More particularly, the invention is used for imaging cells located up to four millimeters or more below the surface of living tissue.

2. Description of the Related Art

Optical coherence microscopy (OCM) is a technique developed recently to image objects embedded in an opaque medium (e.g., flesh) up to a depth of 1 to 2 mm. It has been applied successfully on a prototype basis in ophthalmology (Swanson et al., 1993) and dermatology (Schmitt et al., 1995) to image tissue structures and interfaces. Moreover, OCM has been used to measure the optical properties of tissue and thereby provide information on the physiological state of tissue. OCM has recently become a subject of interest for the study of developmental biology.

Understanding of developmental mechanisms has come from studies of gene expression patterns, tissue geometry, and/or cell morphology, all performed on fixed tissue. From these "snap-shot" views, researchers must infer the dynamics of the underlying cellular and molecular events. Recently, biological imaging technologies have been introduced that permit the non-destructive analysis of cell migration, differentiation, and neuronal interconnection during embryonic development. For example, fluorescent or absorbing compounds can be used to label cells which are then followed with a conventional light microscope equipped with a video camera or with a confocal microscope. The confocal microscope adds significant depth resolution, offering the possibility of obtaining a three-dimensional image by combining optical sections through the depth of an embryo. The image formation rate of the confocal microscope is sufficiently fast to follow the dynamic behaviors of cells as they migrate or of retinal cell axons as they extend, actively sense, and retract projections toward cells in the tectum (O'Rourke et al., 1994). However, light scattering in embryonic tissue reduces the signal-to-noise ratio of a confocal microscope, limiting the depth of the specimen that can be explored to about 200 $\mu$m (Schmitt et al., 1994b). A second imaging technology is magnetic resonance imaging (MRI), recently extended to the microscopic domain so that it can now resolve a 12 $\mu$m cube in living embryos (Jacobs and Fraser, 1994). Although an MRI microscope is indifferent to optical opacity, it is both expensive and slow, requiring nearly an hour to generate a high-resolution image.

It is worth noting that other recently developed imaging techniques also experience image degradation with depth into tissue. For example, green fluorescence protein (GFP) has been modified and expressed in the plant *Arabidopsis thaliana*, yielding beautiful images of developing roots. However, the images are obtained with a confocal microscope and are limited to depths less than 100 $\mu$m in this preparation. Development of the primary meristem in the seed embryo occurs several hundred micrometers into the tissue, too deep for confocal microscopy. Similar limitations apply to 2-photon microscopy (Potter et al., 1996) and fluorescence resonance energy transfer (Helm and Tsien, 1996).

Optical Coherence Microscopy

An optical coherence microscope uses the principles of confocal microscopy, with an additional coherence gate that excludes back-scattered light from out-of-focus planes, resulting in a signal-to-noise ratio that is enhanced by 6 orders of magnitude (Izatt et al., 1994a,b). A resolution of 10 $\mu$m has been achieved in both the lateral and depth directions (Huang et al., 1991b). Optical fiber and solid state sources/detectors are typically used, so the instrument is inherently rugged. OCM overcomes the depth limitation of confocal microscopy and is currently faster than MRI. And at an estimated cost of under $10,000 the instrument is two orders of magnitude less expensive than the MRI microscope.

The coherence gate in OCM is achieved by superposing a Michelson interferometer on the confocal microscope. Back-scattered light from the specimen interferes coherently with light returning from an added reference arm only when the two optical paths are equal. The amplitude of interference fringes (their "visibility") becomes the signal; this signal is appreciable only for light back-scattered from a narrow range of depths in the specimen. The depth range over which interference occurs is related to the coherence length of the source. For example, the depth range, which is also the depth resolution, is roughly 10 $\mu$m when the spectral width of the source is 30 nm ($\lambda$=830 nm, Swanson et al., 1992). At a particular depth, a lateral image (optical section) can be formed by translating the beam; the spot size of the focused beam (easily less than 10 $\mu$m) determines the lateral resolution.

History of Reflectometry

When optical fibers were introduced into the communications industry in the 1970s, the need immediately arose for a method of testing and locating flaws in fiber cables. The first reflectometers (Barnoski and Jensen, 1976), which operated in the time domain, simply measured the round trip time of flight to a reflecting fiber flaw. Typical pulse widths were a few nanoseconds, so spatial resolution was about one meter.

In the 1980s there appeared low-coherence reflectometers which operate in the frequency domain (Danielson and Whittenburg, 1987; Takada et al., 1987; Youngquist et al., 1987). In this technique a spectrally broad (30 nm) light source operating in the near infrared (800 to 1300 nm) is employed in a Michelson interferometer, one leg of which is the fiber under test. The light source has a coherence time of 70 femtoseconds, a considerable improvement over the timedomain pulse widths. As the reference path length is varied, the interferometer output is monitored for interference fringes that occur when light is reflected or back-scattered from a point a distance along the tested fiber equal to the reference path length. The spatial resolution along the tested fiber is one-half the coherence length because the fiber is traversed twice in that leg of the interferometer. (Actually the geometrical spatial resolution is even smaller by a factor of n, where n is the refractive index of the fiber.) For a spectral width of 30 nm, the geometrical spatial resolution along a fiber is 7 µm.

Shortly thereafter ophthalmologists adapted this low-coherence reflectometer to measure the length of the eye (Fercher et al., 1988; Hitzenberger, 1991). Finally lateral scans were added, and both lateral and depth data were interpreted in terms of images of the sample, usually 2-D images with one lateral and one depth dimension (Huang et al., 1991 a,b). The image presumably represents the spatial variation of the optical properties of the sample, primarily the scattering coefficient.

Polarization Effects

Interference occurs at the output of the OCM only between the same polarization components of the electric fields returning from the reference mirror and the sample, respectively. Birefringence effects in the optical fibers or in the sample may alter the relative magnitude and phase of the two polarization components emitted by the source and hence reduce the amplitude of the interference fringes at the photodetector. To eliminate problems in the fibers, some workers have used polarization-preserving fibers and linearly polarized light to eliminate polarization-dispersion effects that lead to different optical path lengths for different polarization states (Clivaz et al., 1992). Kobayashi et al. (1991) constructed a polarization-insensitive reflectometer by separating the two polarization states at the output of the interferometer and measuring their interference fringes with two independent detectors. The sum of the detector outputs is independent of birefringence effects in the fibers or the sample. On the other hand, Wang et al. (1994) devised a simple, inexpensive means of circumventing birefringence effects. They judiciously twist the reference fiber, introducing stress birefringence, until the polarization states of the reference and sample fields are matched and the amplitude of the interference fringes is maximized. Rather than compensate for and eliminate birefringence effects, Hee et al. (1992) have constructed a low-coherence reflectometer to exploit polarization changes in the sample. With this device they were able to measure the birefringence properties of a calf coronary artery.

SUMMARY OF THE INVENTION

The present invention provides a high resolution optical coherence microscope system for visualizing structures below a surface of a biological sample. The system includes a light source emitting light in a wavelength of between 700 and 1500 nm, the light being directed along a sample path and a reference path. The length of at least one of the paths is a modulated path having a selected amplitude of modulation that is equal to or less than about 3 fringes of the wavelength. The modulation may occur at a frequency of at least about 50 kHz, 100 kHz, 300 kHz or at a higher frequency. The light directed along the sample path may scan the biological sample, the scan resulting in an image of a portion of the biological sample; the portion may be between about 100 µm and about 4000 µm below the surface of the sample.

The image may include one or more layers. Each layer may be derived from multiple voxels all corresponding to substantially the same depth below the surface of the sample. The image may include at least about 50 distinct layers, each of the layers derived from a distinct group of voxels, with all voxels for each distinct layer corresponding to substantially the same distinct depth below the surface of the sample. The image likewise may include blended voxels of several layers, such that the image may be a three-dimensional rendering of the portion of the biological sample. The OCM system of the invention further may include a coherence volume about a plane at which the length of the sample is equal to the length of the reference path, such that the coherence volume exists below the surface of the biological sample.

The light from the sample path may enter the sample and taper to a beam waist diameter of not more than 20 µm within the sample. The beam waist is coincident with the coherence volume, such that resolution of structures within the sample is a distance less than or equal to the diameter of the beam waist.

The invention further provides a method of visualizing a structure beneath a surface of a biological sample, employing the OCM system described herein. The OCM system also allows a method of analyzing a biological function based on visualization of in vivo changes in structures beneath a surface of a biological sample. The function to be analyzed may include, for example, gene regulation, development, messenger response, and stress.

The invention also provides a method of visualizing a structure beneath a surface of a biological sample. The method may include the steps of: providing light having a wavelength between 700 and 1500 nm; dividing the light into a sample light path and a reference light path; modulating the length of at least one of the light paths at an amplitude no greater than about 3 fringes of the wavelength; directing light from the sample path into the biological sample, such that the light tapers to a beam waist at a selected depth below the surface of the sample, and such that the beam waist is coincident with a coherence volume about a plane of equal path length of the sample path and the reference path; and detecting an image at the selected depth below the surface of the sample to visualize the structure.

In accordance with this method, the directing step may be repeated at least 100 times, and after each directing step, the method may include the additional step of translocating the sample light path to a different position in the biological sample. The image thus visualized may indicate a difference between a mutant biological sample and a non-mutant biological sample. The image may include a pattern of light scatter, wherein the pattern correlates with a characteristic of the biological sample, such as, for example, gene activity, differentiation, cell elongation, cell dormancy, stress response, and pathogen response.

DETAILED DESCRIPTION OF THE PREFERRED EMBODIMENT

Figure 1:
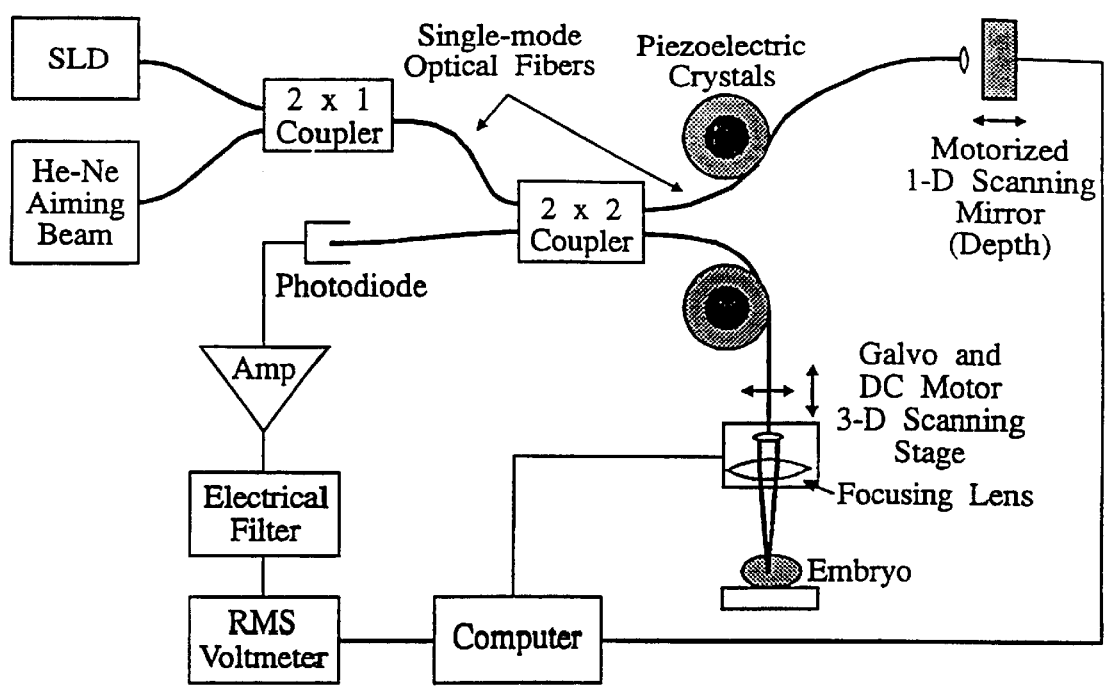
FIG. 1 presents the optical schematic of a fiber-optic optical coherence microscope (OCM).

The present invention discloses an optical coherence microscope capable of addressing fundamental problems in developmental biology. Results for two exemplary developmental systems, the frog *Xenopus laevis* and the plant *Arabidopsis thaliana*, are presented herein. The invention is likewise suitable for application to numerous other taxa including, for example, Drosophila, zebrafish, and virtually any agriculturally or scientifically important plant. The present invention is also broadly applicable to other biological systems wherein the events, structures, cells, and/or processes to be visualized are not accessible to light microscopy. The invention is particularly suitable for developmental biology studies of structures and events within 4 mm, preferably within 3 mm, more preferably within 2 mm, and most preferably within 1 mm, of a tissue surface. Likewise, the invention contemplates use of the disclosed OCM for other purposes, such as, for example, diagnostics and functional genomic analysis. Following the methods disclosed herein, data for a three-dimensional image formed by stacking successive lateral images from different depths can be acquired in less than a minute. Accordingly, the present invention is particularly well suited for high throughput functional genomic analysis, each OCM having the capability of tracking development and other gene-regulated events in many plants per day. In this aspect of the invention, 25, 50, 100, 250, 500, or more plants may be screened per day, depending on the nature of the screening.

Developmental Biology—*Xenopus laevis*

The resolution of the OCM makes it ideally suited for following development within amphibian embryos, where single cell size is typically greater than 10 μm and critical developmental events take place within the first few hundred micrometers. More conventional microscopy (confocal microscopy, video microscopy) is not suitable for following much of the embryonic development because of the highly scattering nature of the frog embryo cytoplasm and the optical aberrations inherent in confocal imaging deep into tissues (Schmitt et al., 1994b). Recently, using an MRI microscope, Jacobs and Fraser (1994) were able to follow events within the interior of a frog embryo during gastrulation and neurulation. Surprisingly, they observed that the deeper cells (mesoderm) and the surface cells (ectoderm) extended at different rates. Previous analyses performed on explanted fragments of embryonic tissue had suggested that the ectodermal and mesodermal tissues extended the embryonic axis roughly in concert (Keller, 1986). It is desirable to examine the exact relationships between these tissues as it is largely believed that signals flowing from the mesoderm to the ectoderm play a primary role in the establishment and patterning of the embryonic nervous system.

Developmental Biology—*Arabidopsis Thaliana*

The plant body is predominantly formed post-embryonically through the activity of specialized tissues called meristems (Steeves and Sussex, 1989). Current understanding of the molecular mechanisms governing the function and formation of meristems is very limited. Recently however, advances in the understanding of meristem formation have been made through the genetic analysis of the small crucifer *Arabidopsis thaliana* (Mayer et al., 1991; Barton and Poethig, 1993). In Arabidopsis two meristems, the primary root and shoot apical meristems, are formed embryonically, while the secondary (lateral) root and shoot meristems appear post-embryonically. Molecular and genetic approaches have been used in order to identify genes required for the formation of the root meristems (Williams and Sussex, 1995; Laskowski et al., 1995). As a result it is now possible to assign stages to developing lateral root meristems based on their morphological characteristics.

The shoot apical meristem of Arabidopsis lies below the surface, and an embryo of Arabidopsis lies within a layer of pigmented cells. As a result, until now the development in the embryo of the primary root and shoot apical meristems could be visualized only by fixing and sectioning or dissection of the embryo from the maternal tissue. These procedures obviously prevent continuous observation of development within the same meristem.

Post-embryonically, the shoot apical meristem forms the vast portion of tissues and organs in a plant (e.g. leaves). Leaves are directly initiated on the flanks of the shoot apical meristem through an asymmetrical expansion of the meristem, leading to a bulge, which after further unidirectional expansion becomes clearly delimited as a leaf primordium (Steeves and Sussex, 1989). Surgical experiments have demonstrated that previously initiated leaf primordia have an inhibitory effect on the positioning of the subsequent primordium, causing it to form on the point farthest from the two previously initiated leaves (Snow and Snow, 1962). Whether this inhibitory effect is due to chemical or physical factors is still unclear (Smith and Hake, 1992; Hernandez and Green, 1993; Green, 1994). Traditional approaches to study phyllotaxy (the pattern of leaf initiation) have required some sort of dissection to remove overlying tissues in order to see the shoot apical meristem. Use of OCM to follow non-invasively the pattern of leaf initiation in Arabidopsis avoids altering the biochemical and physical environment of the plant. It is possible to view processes in the apical meristem, shoot apex, and other deeply buried tissues and organs. For example, OCM permits detection of organ initiation, dorsoventrality, and other processes deeply buried in 1 to 2 millimeters of tissue at a resolution of at least 10 μm. These dimensions fall within the optimal ranges of OCM and are not suited for analysis by other techniques. As one example, OCM permits observation of altered patterns of phyllotaxy arising from genetic mutations or exogenous application of hormones. Furthermore, a high amount of backscattered light detected in cells and tissues by OCM correlates strongly with cells and tissues known to be active in transcription and differentiation. Hence OCM provides a tool to follow any active process, natural or induced in vivo. The present invention thus expressly contemplates uses of OCM embodiments of the invention in various approaches to following active biological processes including, for example, functional genomic analysis, developmental studies, tracking responses to biological signals such as hormones and pathogen elicitors; and the like.

Optical Coherence Microscope

The microscope of the invention is capable of imaging cells located below the surface of living tissue, even though light scattering in the specimen would render it opaque to a conventional or confocal light microscope. Depth penetration is achieved by use of a near infrared superluminescent diode light source with a coherence length of 20 μm together with a coherence gate based on a Michelson interferometer. This combination excludes light back-scattered from out-of-focus planes, giving a depth resolution of 10 μm. Lateral resolution of 10 μm or better is achieved by focusing the illuminating beam down to a small spot. Two-dimensional lateral scanning of the beam spot produces an optical section at a fixed depth in the sample. A three-dimensional image is obtained by stacking successive optical sections at different depths. Such three-dimensional scans typically take less than a minute.

FIG. 1 presents the optical schematic of a fiber-optic OCM. The superluminescent diode (SLD) is a laser diode with end facets that have been anti-reflection coated so that no lasing occurs, and hence the full spectral breadth of the transition appears in the output. The center wavelength lies in the near infrared (e.g., 850 nm) where the absorption coefficient of biological tissue is near its minimum. Assuming a Gaussian spectral profile, a 30 nm fill-width-at-half-maximum (FWHM) spectral width of the SLD yields a final depth resolution (FWHM of the Gaussian visibility function) of 11 µm/n , where the refractive index, n, of tissue is close to 1.40 (Bolin et al., 1989). The helium-neon laser beam (633 nm) serves simply to visualize the focused spot, and both beams are coupled into single-mode optical fibers. The two fibers are combined in a fused region called a "2×1 coupler".

Each source beam is split and sent along the two paths of the Michelson interferometer by the 2×2 coupler, a similar fused region of two fibers that mixes their spatial modes. The sample path fiber is terminated with an aspheric collimating lens, and the beam is then focused by a doublet lens to a spot diameter of 9 µm. The sample fiber/focusing lens assembly is mounted on a 3-D scanning stage consisting of a 1-D translation stage powered by a DC motor and a pair of galvo-scanners in an x-y mount. The closed-loop galvo-scanners raster-scan the horizontal plane while the closed-loop DC motor steps along the depth dimension, so the waist of the focused beam explores a sample volume and an OCM image is formed. The reference path fiber is also terminated with an aspheric collimating lens and is led to a reference mirror (retroreflector) that is mounted on another translation stage driven by a closed-loop DC motor. As the sample fiber/focusing lens assembly is stepped along the depth dimension, the reference mirror is translated to keep the beam waist coincident with the coherence volume (position of equal path lengths in the interferometer). This last point is important because the Rayleigh range of the focused beam is roughly 60 µm, so the beam rapidly expands and the lateral resolution quickly degrades as the coherence volume deviates from the beam waist.

In one embodiment, the instrument may also include matching piezoelectric cylinders around which are wrapped the reference path fiber and the sample path fiber. In response to an applied voltage the circumference of each cylinder changes slightly, resulting in a change in the optical path length of the fibers. If the piezoelectric cylinders are driven (180° out of phase) by a triangular voltage signal with a frequency of, for example, 8.3 kHz, the resulting changes in the fiber lengths modulate the optical path length difference between the two arms of the interferometer. If the amplitude of the piezo-driving voltage is chosen so that the optical path length variation is ±1.5 $\lambda$, the interference pattern at the interferometer output will be modulated at 100 kHz, a frequency that is easily isolated by an electrical bandpass filter to increase the signal-to-noise ratio. Alternative embodiments may employ a piezoelectric stack with a mirror attached thereto as a way of achieving high frequency length changes in a light path. That embodiment is described in more detail in Example 1 below.

Scanning Techniques

Two different general methods can be used to scan a sample and create an OCM image. First, one can perform a 2-D lateral scan at a fixed depth, then increment the depth, then perform another lateral scan, etc. A 3-D image of a sample volume is then constructed by successively stacking 2-D optical sections that are parallel to the surface of the sample. In contrast, most researchers (see, for example, Huang et al., 1991 a) perform a longitudinal (depth) scan at a fixed transverse point, then translate the beam laterally in a single direction and repeat the longitudinal scan, etc. Typically a 2-D optical section is then formed which is perpendicular to the sample surface, having one depth dimension and one lateral dimension. Each longitudinal scan is accomplished by translating the reference mirror at speeds as high as 160 mm/s (Hee et al., 1994). The light reflected from the moving reference mirror is then Doppler shifted by as much as 380 kHz, and the electrical bandpass filter can be set at that frequency. In this case there is no need for the modulation of the interference pattern provided by the piezoelectric crystals included in FIG. 1. However, with this Doppler-shift technique it is difficult to keep the beam waist coincident with the coherence volume, resulting in degraded lateral resolution. For the imaging of embryos, it is preferable to scan in both lateral directions to create an optical section at a given depth.

Focusing the Beam

The lateral resolution of an OCM image is determined by the size of the focused beam. Thus, for good resolution, it is beneficial to use a focused spot less than 10 µm in diameter. In one embodiment of the OCM (see FIG. 1), the sample fiber is terminated with an aspheric collimating lens (f=6.2 mm, OZ Optics) so that the emerging beam has a $1/e^2$ diameter of 1.4 mm and a divergence half-angle of 0.4 mrad. The subsequent focusing doublet lens (f=10 mm, Melles Griot, 06LAI001) is designed to minimize spherical aberration at 830 nm and yields a nearly diffraction-limited spot size with a $1/e^2$ diameter of 8 µm.

Figure 2:
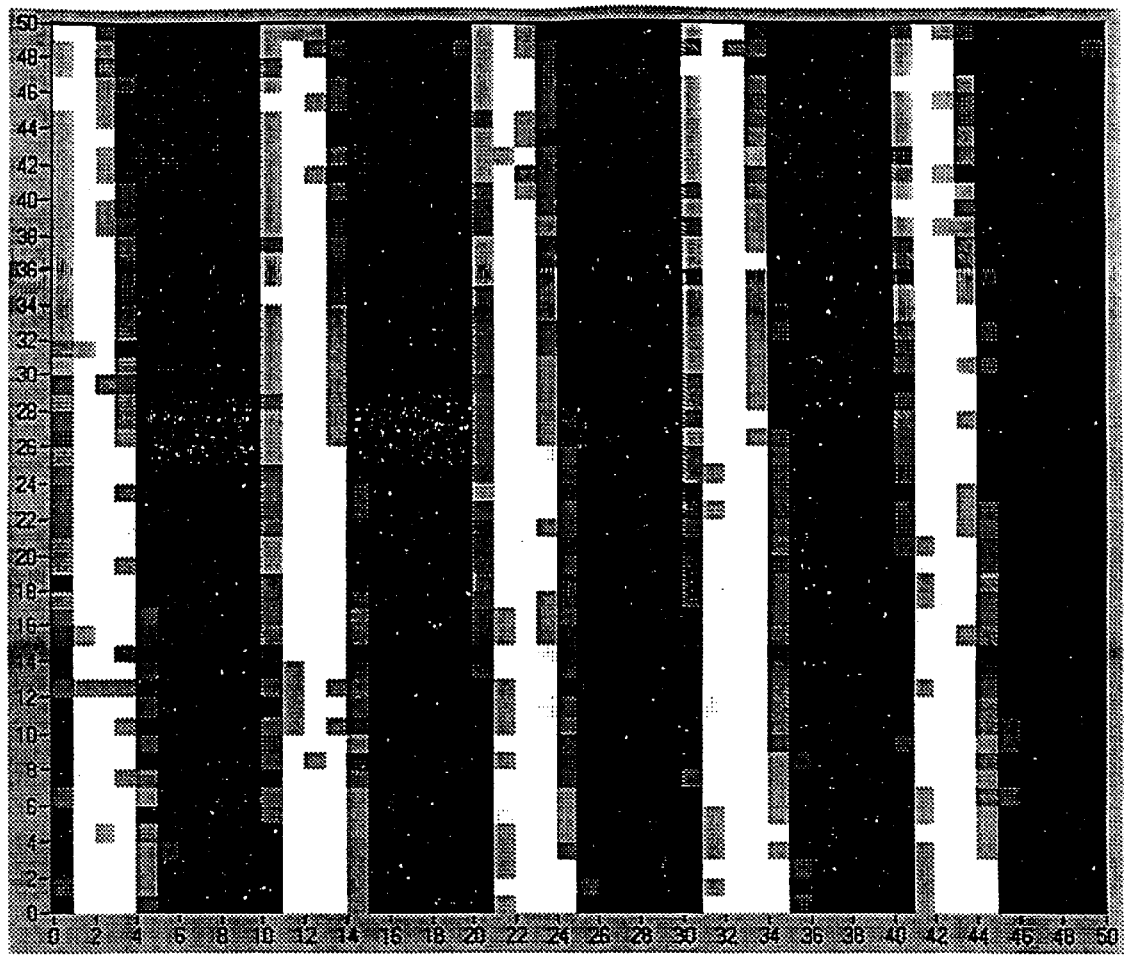
FIG. 2 is an image of a Ronchi ruling visualized through 1.2 mm of a highly scattering solution of polystyrene latex spheres.

A selected focusing arrangement can be tested by imaging a Ronchi ruling through 1.2 mm of a highly scattering solution of polystyrene latex spheres. The Ronchi ruling consists of 10 µm wide stripes of chrome deposited on a glass cover slip. The chrome stripes are separated by 10 µm stripes of clear glass. The highly scattering solution serves as a tissue phantom and consists of 0.523 µm diameter polystyrene latex spheres. The solution has a scattering coefficient $\mu_s$, of 40/cm and a reduced scattering coefficient $\mu_s'=(1-g)\mu_s$ of 10/cm where the asymmetry parameter g equals the mean cosine of the scattering angle. The sphere solution represents nearly 5 optical depths and appears opaque to the unaided eye or through a conventional microscope. From a detailed analysis of images like FIG. 2, the $1/e^2$ diameter of the beam waist was determined to be 8.8±0.2 µm, just slightly larger than the diffraction-limited spot size of 8 µm.

Image Acquisition Time

In designing and constructing an OCM for imaging in developmental biology and biotechnology, a critical factor is the time needed to acquire an image. Certainly this time should be short compared to the mean time between cell divisions, and it would be helpful if the acquisition time were short enough to eliminate gross motion of the embryo. The fundamental physical phenomenon that places a minimum on the acquisition time is photon noise. For example, to obtain 3% precision in the collected signal at each voxel in a 3-D image of an embryo, assuming Poisson statistics, there must be about $10^3$ photons in the collected signal for an average voxel. Thus, to image a 500 µm cube at a resolution of 10 µm in each direction, and a scan step of 5

μm in each direction, then data must be collected from 100×100×100=10⁶ voxels. The total number of photons required is therefore $10^6 \times 10^3 = 10^9$ photons.

The collected signal is proportional to the amplitude of the interference fringes at the output of the interferometer. The interference term is proportional to the electric field back-scattered from a voxel, so the collected signal is proportional to the square-root of the back-scattered power (Izatt et al., 1994a). If $P_o$ is the power incident upon the interferometer, and P(z) is the power returning from a voxel at depth z, then:

$$\text{signal} \alpha \ P_o \ \text{sqrt}(P(z)/P_o) \quad (1)$$

Interpretation of OCM Images. Although several OCM images of living biological tissue have been reported in the literature (Swanson et al., 1993; Hee et al., 1994; Schmitt et al., 1994c,d, Bouma et al., 1995), a great deal of work remains to be done in identifying the precise optical characteristics of the sample that give rise to features in the OCM image. Schmitt et al. (1993, 1994a) have shown that in weakly scattering media the power returning from a sample volume at depth z in an OCM instrument is given by $$P(z) = P_o \exp(-2\mu_t z) \cdot \mu_{back} l_{coh}/2 \quad (2)$$

where $P_o$ is the power incident upon the interferometer, $\mu_t = \mu_s + \mu_a$ is the total attenuation coefficient equal to the sum of the scattering and absorption coefficients of the medium (units of 1/m), $\mu_{back}$ is the back-scattering coefficient (1/m), and $l_{coh}$ is the coherence length of the source. In equation (2), $P_o \exp(-\mu_t z)$ is the power reaching a depth z in the sample without being scattered or absorbed, $\mu_{back} l_{coh}/2$ is the fraction of that power that is back-scattered and can coherently interfere at the output of the interferometer, and $\exp(-\mu_t z)$ is the fraction of the back-scattered light that reaches the surface of the medium without being scattered or absorbed. As pointed out by Schmitt et al. (1993), OCM data can be used in conjunction with equations (1) and (2) to deduce values for $\mu_t$ and $\mu_{back}$ in tissue. Indeed, Clivaz et al. (1992) have used OCM to measure the scattering properties, refractive index, and thickness of arterial walls.

Schmitt et al. (1994a) used Monte Carlo simulations to show that the single-scattering model of equation (2) is valid in a medium up to 4 or 5 optical depths (4 or 5 /$\mu_t$). Using OCM, Schmitt et al. (1993) measured $\mu_t$ to be about 5/mm (and $\mu_{back}$ to be about 1.5/mm) in the dermis of the human finger and forearm. At greater than 4 to 5 optical depths, multiple scattering begins to become important, and resolution may be degraded. On the other hand, Izatt et al. (1994a) show that OCM has its greatest advantage over confocal microscopy between 5 and 15 optical depths.

Schmitt et al. (1994c) studied the walls of freshly excised rat coronary arteries with OCM. Using focused beam spots with diameters ranging from 8 to 17 μm, they measured higher total attenuation coefficients with larger beam spots. They concluded that the increase in measured $\mu_t$ was a result of degradation of spatial coherence across the beam with increasing beam diameter. They speculated that this degradation was due to spatial fluctuations in the refractive index in the artery walls, and suggested a theoretical framework based on the mutual coherence function of the beam that might begin to describe quantitatively the observed loss in spatial coherence.

A thorough interpretation of OCM images of biological tissue requires an elucidation of the origin of scattering and absorption in tissue. For example, one can imagine two types of scattering from a cluster of cells: (1) scattering from cell organelles which should lead to scattering over all scattering angles, perhaps slightly weighted toward forward angles, and (2) Fresnel reflections from refractive index mismatches such as might occur at the extracellular/intracellular interface. The latter scattering should be highly directional and is referred to as the "specular" reflection. Of course both types (1) and (2) arise from inhomogeneities in the refractive index, but the angular dependence is quite distinct. Moreover there is a phase change of 180° in type (2) scattering when the reflection is from a medium with a higher refractive index.

Calibration of the OCM

It is desirable to devise numerous calibration procedures for the OCM. One important calibration procedure is to use the OCM to examine tissue phantoms with carefully constructed optical properties and physical dimensions. For example, the longitudinal scan of an OCM can be tested by examining phantoms consisting of homogeneous layers of highly scattering solutions with depths defined precisely by microscope cover slips. The solutions can be made of polystyrene latex spheres or Intralipid, a fat emulsion used for intravenous feeding in hospitals. The spheres are available in precise diameters; Mie theory can be used to calculate the scattering coefficient of sphere solutions as well as the asymmetry parameter g, the mean cosine of the scattering angle. Intralipid contains a wide continuum of particle sizes, but its optical properties have been studied exhaustively because it is less expensive than the latex spheres (Driver et al., 1989; Flock et al., 1987, 1992; van Staveren et al., 1991). Values for $\mu_t$ for solutions of spheres and Intralipid can be measured with a spectrophotometer using a successive dilution technique.

Lateral and depth resolution can be checked by placing a resolution target or a microscope calibration reticle at an interface between layers in a tissue phantom. (See the image of a Ronchi ruling in FIG. 2.) Slopes, intercepts, and discontinuities in data from a longitudinal scan can be used to deduce $\mu_t$ and $\mu_{back}$ for the various layers in a phantom (Schmitt et al., 1993). Longitudinal scans of a solution of polystyrene spheres (used also in FIG. 2) showed that measured fringe visibility falls off exponentially with depth as predicted by equation (2), and a value for $\mu_t$ of 38.4±0.2 /cm. A series of spectrophotometer measurements yielded $\mu_t$ of 40.0±0.1 /cm. The discrepancy is probably due to the small contribution of multiply-scattered photons.

Images from the OCM

Image acquisition may be directed by a computer system running visualization software such as, for example, LabView (from National Instruments). As an example, an image may consist of 500,000 voxels and cover a volume of 1 mm×1 mm×1 mm. Of course, the invention may be applied to images of any number of voxels, whether fewer than 500,000 voxels or more than many millions of voxels. Desired voxel number will be selected based on the volume to be imaged and the resolution desired. Horizontal slices of images may be viewed during data acquisition, and after collection a 3-D image can be viewed quickly as a time series of horizontal slices displayed on a computer monitor. More extensive examination of a 3-D image may be accomplished by transferring the image to a Unix workstation running an advanced software package such as, for example, AVS 5.0 (Advanced Visualization Systems). A particularly useful way to extract information from an image is to rotate a volume rendering of the image, noting alignment of structural features. In a volume rendered image, the contribution of a voxel at the rear of the image volume is "blended" with contributions from all voxels along the line projecting forward to the final pixel in the 2-D image. Several of the Figures included herewith are simply volume-rendered images viewed from a single perspective, then printed on a color laser printer. The information content of these laser printer images is significantly less than the rotating volume-rendered images on the computer monitor.

Optical Properties of Frog and Plant Tissue

Figure 3:
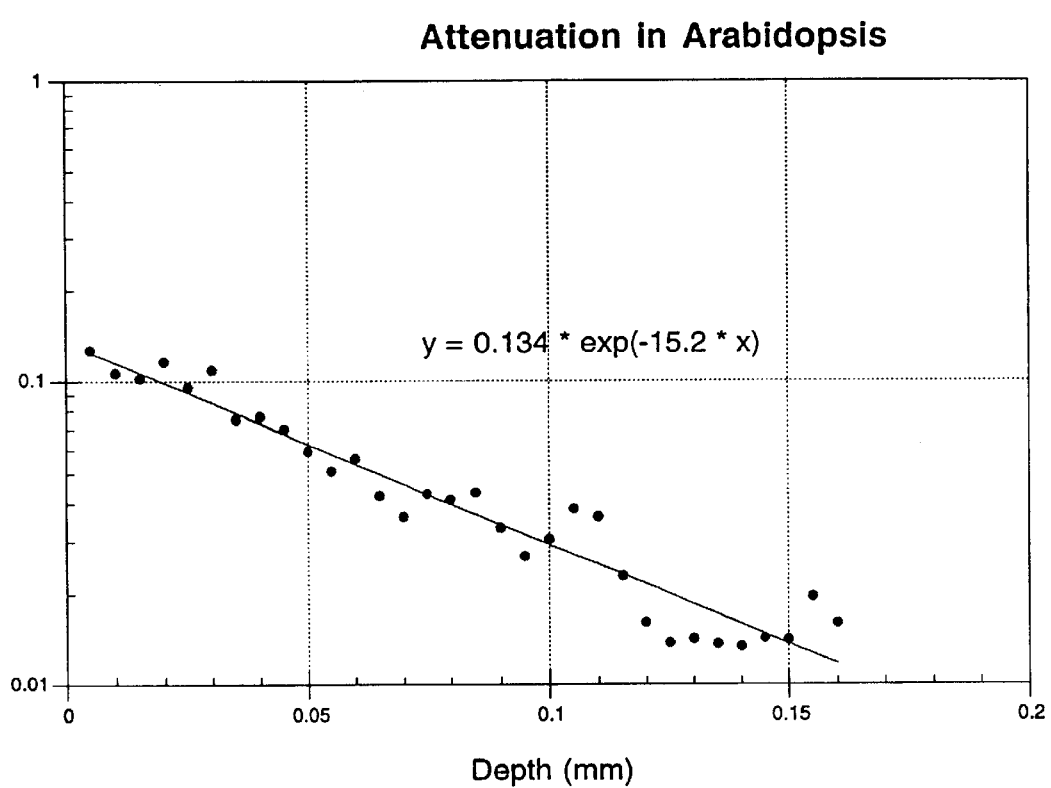
FIG. 3 is a typical plots of OCM fringe amplitude versus depth, averaged over horizontal slices in a plant preparation.
Figure 4:
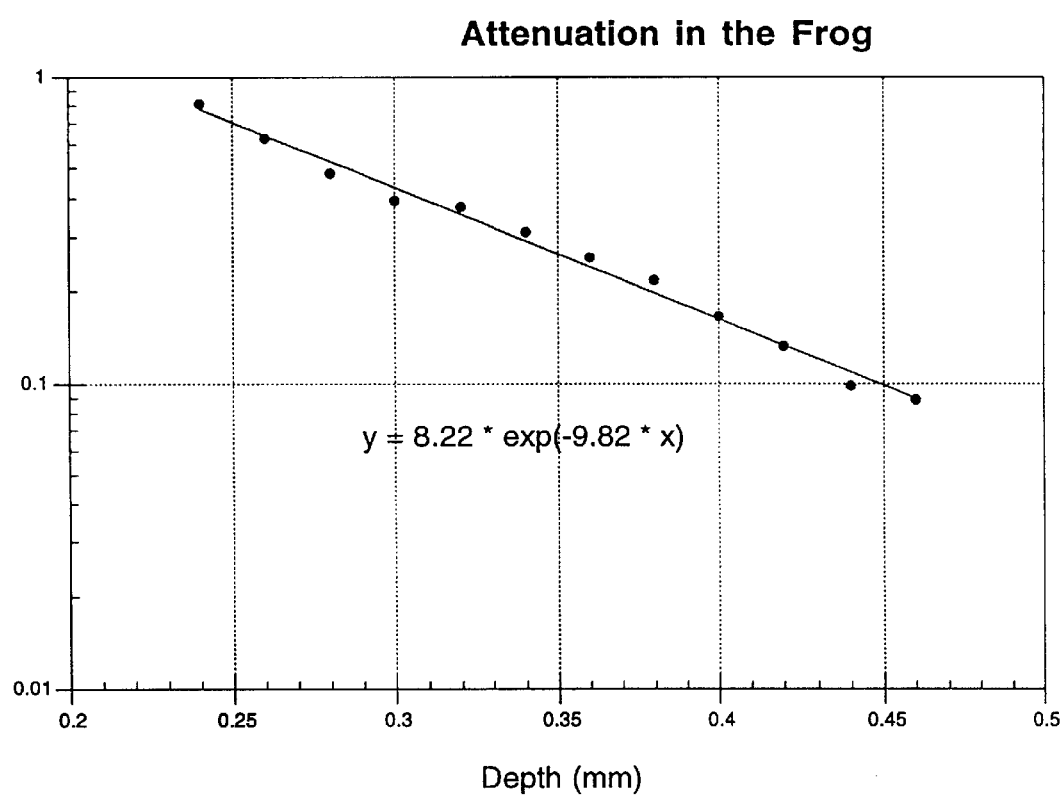
FIG. 4 is a typical plots of OCM fringe amplitude versus depth, averaged over horizontal slices in a frog preparation.

From the images collected of frog and plant tissue, average values have been deduced for the total attenuation coefficient $\mu_{total}=\mu_s+\mu_a$ where $\mu_s$ and $\mu_a$ are the scattering and absorption coefficients. As the 850 nm beam enters the sample, the incident power is attenuated with depth due to scattering and absorption. FIGS. 3 and 4 are typical plots of OCM fringe amplitude versus depth, averaged over horizontal slices in plant and frog preparations, respectively. Fringe amplitude is proportional to the square-root of power backscattered from the sample, so it should decay exponentially with depth according to $\exp(-\mu_{total}$ depth). Fitted values for $\mu_{total}$ are 15 and 10/mm for plant and frog tissue, corresponding to optical depths (l/e attenuation lengths) of 70 $\mu$m and 100 $\mu$m, respectively.

Design of the Modified OCM

The modified OCM is faster than the original instrument because the x-y scans are performed by galvo-scanning mirrors instead of DC motor translators. In addition, a piezo-mounted reference mirror produces output fringes at 125 kHz instead of the 2 kHz frequency achieved by wrapping optical fiber around a piezo-cylinder.

Other modifications to the OCM are contemplated by the invention. For example, a lower response time for the electrical filters that selectively pass the first two harmonics of the fringe frequency can be achieved by widening the bandpass of these filters. In addition, the rms integrated circuit that may be used to measure the amplitude of the fringe signal has an inherently low dynamic range. Digital signal processing (DSP) is therefore a desirable alternative to analog circuits. A DSP solution can permit modifications to the filter characteristics in software, with the response time to be determined by the integer number of fringe periods that are sampled. The dynamic range thus can be improved over the analog rms chip because multiplications are performed digitally.

Figure 5:
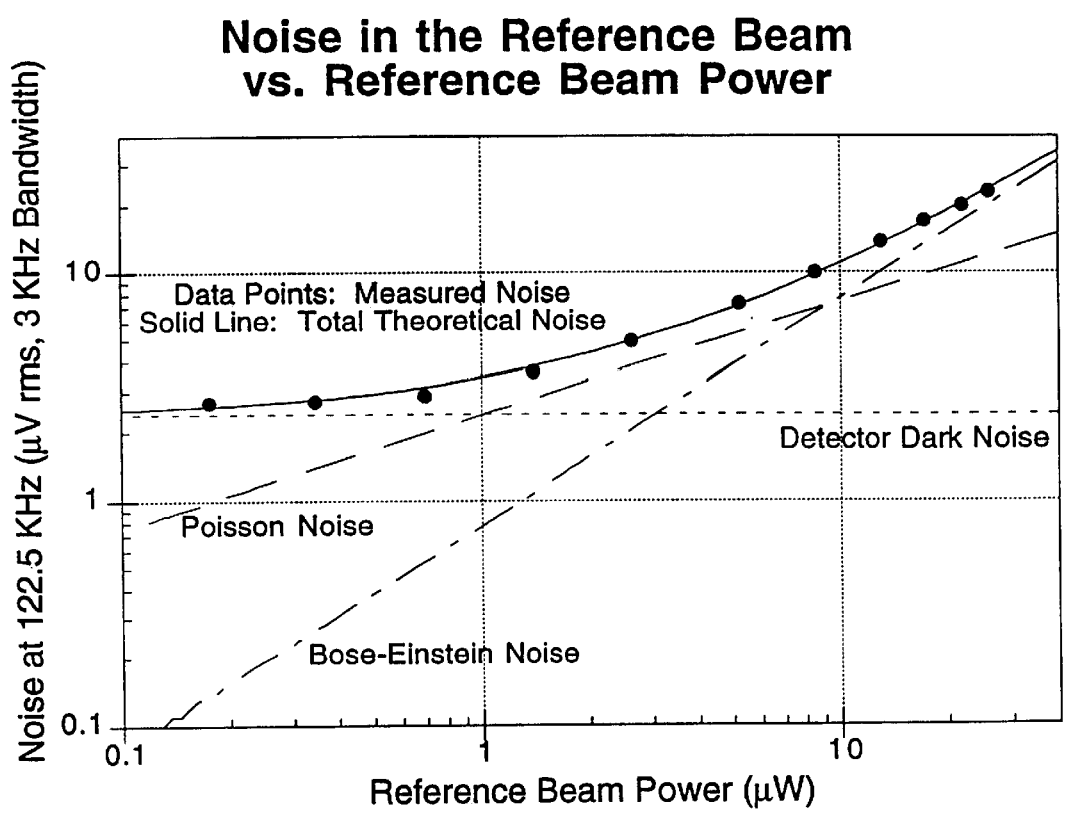
FIG. 5 illustrates that relationship between noise in the reference beam versus reference beam power.

In addition, photodetector noise at 100 kHz is 25 pW/sqrt (Hz), a factor of 8 greater than the manufacturer's specification (New Focus, Model 1801). By substituting a similar silicon photodiode/amplifier hybrid from Advanced Photonix (Model SD 100-41-21-23-1) a noise level of 1 pW/sqrt (Hz) was achieved. The amplifier in the Advanced Photonix photodetector has a bandwidth of 400 kHz compared with 125 MHz for the New Focus detector. Also, the Advanced Photonix photodiode operates with a reverse bias of 15 Volts, while the New Focus diode has no bias. This reduction in photodetector noise reduced overall noise levels to the rage of fundamental photon noise. FIG. 5 illustrates that the typical OCM interferometer output of 25 $\mu$W is accompanied by photon noise that is primarily Bose-Einstein. This ultimately means that the OCM achieves its maximum signal-to-noise ratio when the reference beam is cut to 3 $\mu$W.

The low amplitude path length modulations of the invention are important in achieving good axial resolution of the image, consistent with the coherence length of the light source. Desirable amplitudes in path length are most meaningfully expressed as a function of the fringe of the wavelength of the light source being used, where one fringe is defined as ½$\lambda$. An amplitude of about 3 fringes is preferred, an amplitude of about 2 fringes is more preferred, and an amplitude of about 1 fringe or less is most preferred. For example, with a wavelength of 850 nm, 3 fringes=1275 nm, 2 fringes=850 nm, and 1 fringe=425 nm.

EXAMPLES

Example I

Modifications to the OCM System

A. Obtaining high-frequency modulation of path length by attaching a lightweight reference mirror to a piezoelectric stack 1. Fast phase modulation Fast phase modulation was achieved in the Michelson interferometer of the OCM system by attaching a lightweight reference mirror to a piezoelectric stack and driving the stack at a resonance frequency of about 125 kHz. The electrical behavior of the piezo stack and the mechanical properties of the piezo-mirror arrangement were examined. A displacement amplitude at resonance of about 400 nm was achieved using a standard function generator. Slow drifts in the pathlength difference of the two interferometer arms caused variations in the measured rms intensity of the AC-coupled output fringe signal. By driving the piezo stack at an optimal amplitude (a displacement of 0.42 $\lambda$, or slightly less than 1 fringe) and summing the powers in the first two harmonics of the piezo-driving frequency, drift-insensitive measurements of the output fringe signal were achieved.

Piezoelectric crystals are used in a variety of forms for phase modulation in interferometry. The mirror in the reference arm of a Michelson interferometer is often attached to a piezo stack that is driven at frequencies up to 10 kHz, well below its resonance frequency. With driving amplitudes of some ten to a hundred volts, pathlength modulations of the order of a few $\mu$m can be achieved. In fiber optic interferometers, the fiber can be wound in a large number of turns around a hollow piezoelectric cylinder. Driving the cylinder up to frequencies of a few kHz will cause it to expand and contract radially, stretching and relaxing the fiber accordingly and thus providing the modulation of the optical path length. However, this method typically requires tens of meters of fiber, making the interferometer sensitive to thermal fluctuations that result in phase wander of the output fringe signal. Other problems with this approach may include static polarization mismatch and dynamic birefringence modulation, which requires a Faraday rotator for compensation. Fibers coated with piezoelectric films have also been used. When a voltage is applied to the piezo jacket, the fiber is squeezed radially and thus increases in length. In this way, fast phase modulations can be achieved, but the modulation amplitude is typically small. In order to produce a change in optical path length of 1 $\mu$m at 100 kHz, a fiber coated over a length of 20 cm would require more than 100 V of driving amplitude.

In order to minimize the time required to collect an OCM image, it was desirable to develop a method of phase modulation with a frequency greater than 100 kHz and a displacement amplitude of the order of 1 $\mu$m. This Example describes the use of a piezoelectric stack that is driven at a resonance frequency of 125 kHz to produce a displacement amplitude of 400 nm with a peak-to-peak driving voltage of only 6.7 V.

2. Tests of the electrical behavior of the piezoelectric stacks

Piezoelectric stacks manufactured by NEC Corporation of Japan (available from Thorlabs Inc., Newton, N.J., type AE0203-D04) were tested for possible use in the Michelson interferometer of the OCM of the invention. The dimensions of these piezos are 2.5 mm×5 mm×5 mm, and the manufacturer's specifications indicate a displacement of about 3 µm at 100 V DC. Since the impedance of the piezo decreases initially with increasing frequency (Z=1/ωC where C=100 nF), the larger currents necessary to maintain this applied voltage might lead to overheating of the stack at higher frequencies. In any case, a high power function generator would be necessary for operation at higher frequencies. Driving the piezos at their resonance frequency, however, proved to be a method for circumventing these problems.

Figure 6:
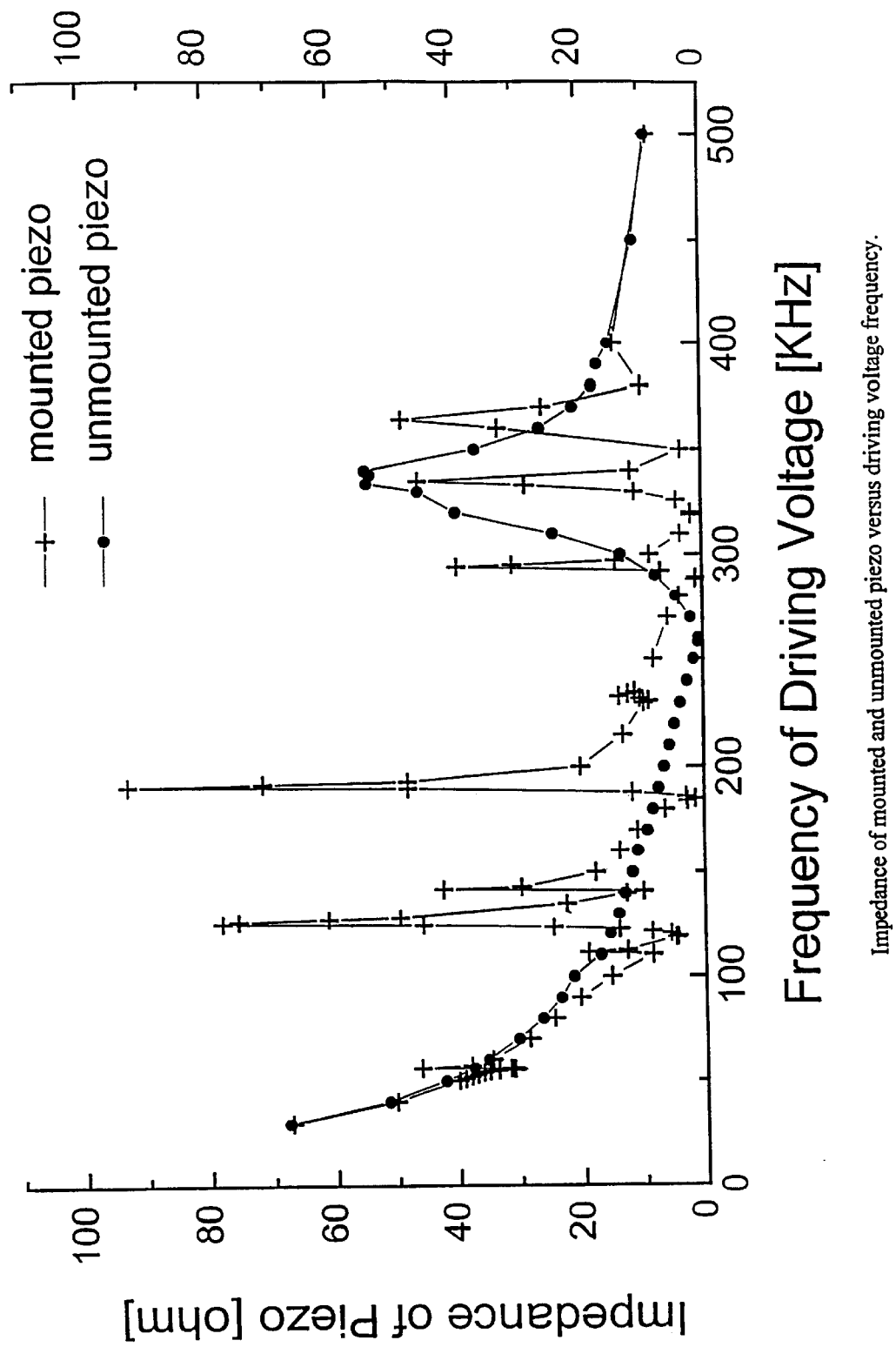
FIG. 6 shows the impedance of mounted and unmounted piezos as a function of the driving voltage frequency.

The electrical behavior of the unmounted piezo was tested by measuring its impedance as a function of frequency (see FIG. 6). At frequencies well below resonance, the piezo behaves like a capacitor, with the impedance inversely proportional to the frequency and the voltage lagging the current by approximately 90 degrees. At 255 kHz the unmounted piezo experiences a minimum in impedance, and voltage and current are in phase. This frequency is commonly referred to as the electrical resonance frequency of the piezo. At 330 kHz a maximum in impedance occurs, and again voltage and current are in phase—the electrical antiresonance frequency of the piezo. Between resonance and antiresonance the impedance increases with frequency, while the voltage leads the current by about 90 degrees. At frequencies higher than the antiresonance, the piezo again shows a capacitor-like behavior.

Several unmounted piezos of the same model were tested, and their electrical characteristics were found to be consistent within a few percent. These measurements were repeated for a different brand of piezo stack with slightly larger dimensions (3.5 mm×3.5 mm×9 mm, from Piezomechanik, Munich, Germany). The same type of behavior was observed, with the impedance minimum and maximum occurring at 153 kHz and at 191 kHz, respectively, hence at lower frequencies than for the smaller NEC piezos.

In order to use the piezo stack for phase modulation, a small, lightweight mirror (1.5 mm×1.5 mm×0.1 mm, from Edmund Scientific Co., Barrington, N.J.) was attached to its face with cyanoacrylate ("super glue"). The piezo stack with the attached mirror was either glued directly onto a standard adjustable mirror mount or glued onto a 25 mm diameter aluminum disk of 5 mm thickness, which was then held by a mirror mount. Although gluing the lightweight mirror to the piezo did not alter its electrical behavior, attaching the stack to the aluminum disk or the mirror mount significantly changed the piezo's electrical resonance characteristics. Instead of the single electrical anti-resonance of the unmounted piezo, several anti-resonances at frequencies both lower and higher than the original one appeared. FIG. 6 also shows the impedance of the mounted piezo as a function of the driving voltage frequency. This piezo had been glued to an aluminum disk with an epoxy intended for fiber optic connectors (F 120, from Thorlabs Inc., Newton, N.J.).

3. Mechanical behavior of the piezo-mirror in a Michelson interferometer

Figure 7:
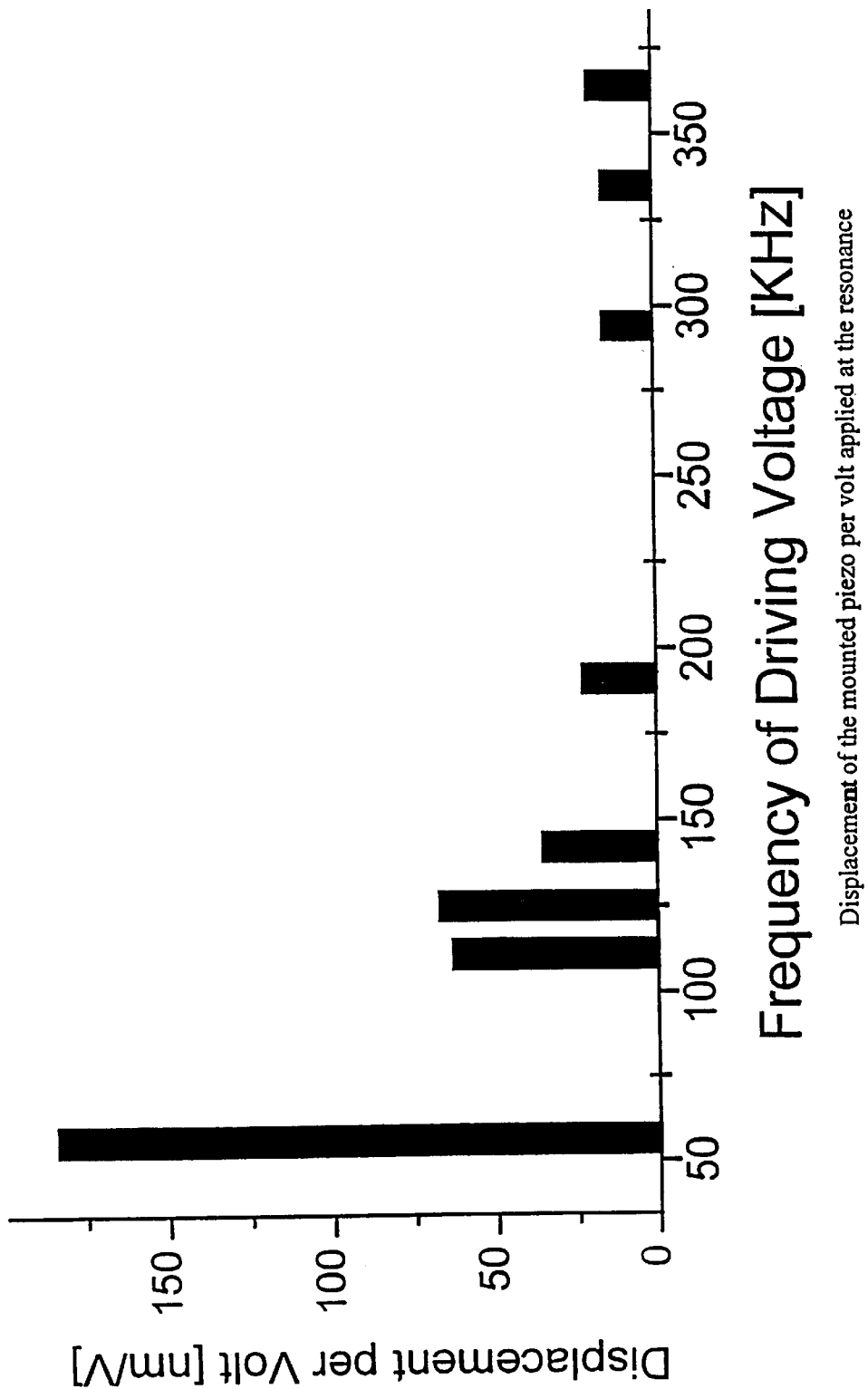
FIG. 7 shows the displacement of the piezo per volt applied at each of the resonance frequencies.

The mechanical behavior of the piezo-mirror was tested in one arm of a Michelson interferometer with a helium-neon laser (633 nm) as a light source. In the measurements with the mounted piezo, it was observed that the frequencies of maximum piezo displacement are those of maximum impedance. The mechanical resonance of the piezo is thus coincident with its electrical anti-resonance. In the following, those frequencies are referred to as resonances for which the piezo experiences a maximum in displacement. FIG. 7 shows the displacement of the piezo per volt applied at each of the resonance frequencies. For a particular resonance frequency, the piezo displacement was observed to increase linearly with increasing driving voltage amplitude. However, the displacement per volt varies for the different resonances of the same piezo and decreases at higher frequencies. Although the displacement per volt is higher at the 56 kHz resonance by almost a factor of three, the piezo in the Michelson interferometer was instead driven at the 125 kHz resonance because of its higher frequency (see Section 5).

Both the positions of the resonances and the corresponding displacement amplitudes were dependent on the details of mounting the piezo in a way that could be understood at least qualitatively. Attaching the stack with super glue resulted in lower resonance frequencies and larger displacement amplitudes than in the case where the softer epoxy was used. This result is interpreted to mean that the very thin layer of super glue between the piezo and the mounting substrate forces the piezo to expand in the free direction only. This results in a larger displacement of the mirror than when a thicker layer of the more elastic epoxy is used, presumably because the epoxy can be squeezed by the expanding piezo. Also, if the piezo mounted with super glue expands primarily in the free direction, its center of mass translates, in contrast with the piezo in epoxy, which may expand and contract about its center of mass. The piezo mounted with super glue then has a greater effective mass as it resonates, yielding lower resonance frequencies.

Similarly, the disk on which the piezo is mounted can play an important role in determining the positions of the resonance frequencies. The difference between epoxy-glued NEC piezos on 5- and 10-mm thick aluminum disks, both of 25 mm diameter, was examined. They exhibited essentially the same resonance frequencies between 100 and 360 kHz, but the lowest resonance, which also has the largest displacement amplitude, was shifted from 56.7 kHz for the thinner to 85.6 kHz for the thicker aluminum disk. Plate theory predicts that the resonance frequency of the lowest (drumhead) mode for a 25-mm diameter, 5-mm thick aluminum disk should be around 80 kHz and a factor of two higher for the 10-mm thick disk. The formula used is valid under the assumptions that the disk is held rigidly at its periphery and that the thickness of the disk is small compared to its diameter. Neither of these assumptions is well fulfilled in the present case. Further investigation using a finite element analysis software package (SAP 2000 Nonlinear V6.15) revealed that the resonance frequencies are very sensitive to the precise mounting conditions, with the observed frequencies roughly consistent with the three-point mounting technique employed in these tests. Measurements with two three-point mirror mounts of different masses yielded the same mechanical resonances and piezo amplitudes. These measurements and calculations support the conclusion that the lowest frequency resonance for the stack-epoxy-disk system is probably a fundamental vibration of the disk, while the higher frequency resonances can be attributed to the "piezo-in-epoxy" part of the system.

The results for resonance frequencies and displacement amplitudes for the same brand of piezo and the same mounting technique for the piezo did not differ by more than a few percent. Operating the piezo-mirror system in the OCM Michelson interferometer for hours at a time over the course of one year has not caused a shift in the resonance frequency or a change in the piezo displacement. Even after hours of continuous operation, the stack does not heat up noticeably, and the system maintains a high degree of stability. With a driving voltage of 6.7 V peak-to-peak, the described NEC piezo with superglue-mounted mirror, epoxy-mounted onto a 5 mm thick aluminum disk, provides a displacement of around 400 nm at a resonance frequency of about 125 kHz, making it ideally suited for phase modulation in the OCM of the invention.

4. Calculations determining the optimum modulation amplitude

The superluminescent diode (SLD) light source in the tested OCM has a wavelength of 850 nm. Therefore, a piezo displacement of 400 nm produces a total pathlength difference between sample and reference arms in the OCM of less than one wavelength ($\lambda$), i.e., modulation is over less than one fringe. For such small pathlength modulations, the interferometer output fringe signal will take on distinctly different shapes depending on the initial phase relation between the sample an d reference beams.

Figure 8:
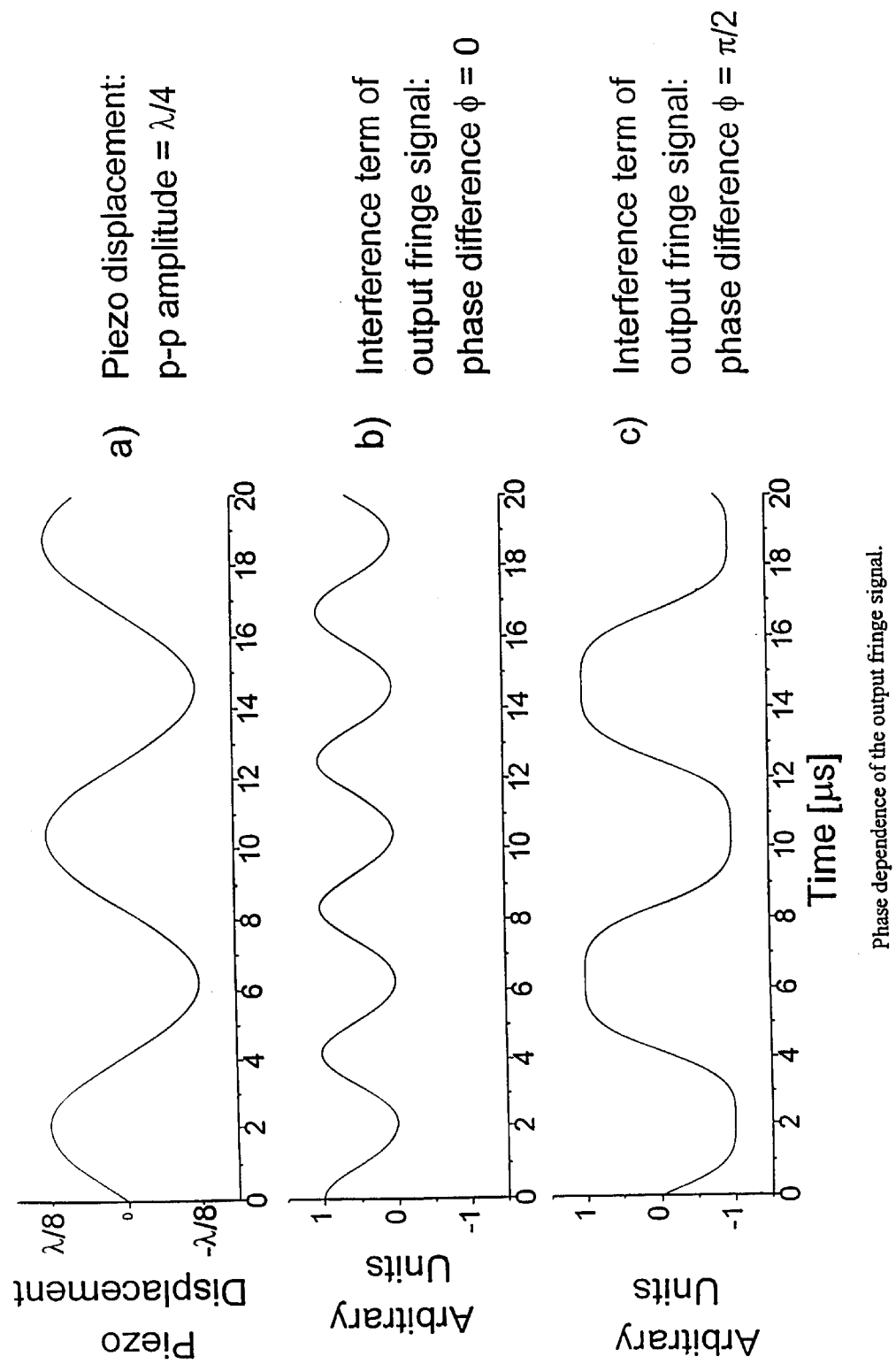
FIG. 8 illustrates the phase dependence of the output fringe signal.

FIG. 8 illustrates this point for a modulation of one-half fringe (piezo displacement of 0.25 $\lambda$). Graph (a) in FIG. 8 shows the piezo displacement which is simply of the form $d_o \sin \omega t$, where the peak-to-peak displacement $2 \text{-} D_o$ is taken to be 0.25 $\lambda$. Theoretically, the interference term in the corresponding interferometer output intensity is given by:

$$I_{out} = I_o \cos(\alpha \sin \omega t + \phi)$$

where $\alpha$ is related to the piezo displacement amplitude by $\alpha = 4\pi d_o/\lambda$, and $I_0$ is equal to 2 $\sqrt{(I_{ref} I_{sample})}$, where $I_{ref}$ and $I_{sample}$ are the intensities returned from the reference and sample paths. Graph (b) in FIG. 8 plots $I_{out}$ for an initial phase difference between the sample and reference beams of $\phi=0$; Graph (c) is a similar plot for $\phi=\pi/2$. The two signals are clearly different in shape and have different Fourier components, including different DC components. In Graph (b) the strongest component is the one at $2\omega$, the second harmonic of the modulation frequency. In Graph (c) the signal's dominant Fourier component is the one at $\omega$, the fundamental of the driving frequency. By inspection of the graphs, it also becomes clear that the rms values for the AC-coupled signals are different. (The interferometer output must be AC coupled in the OCM to eliminate the huge DC component $I_{ref}$.) Therefore random phase drifts between the sample and reference beams will lead to drifts in the rms value of the AC coupled interferometer output.

Calculating the Fourier components of the signal (1), the power $P_1$, in the fundamental frequency $\omega$ and the power $P_2$ in the second harmonic $2\omega$ can be expressed as:

$$P_1 = 2I_0^2 J_1^2(\alpha) \sin^2\phi \quad (2)$$

$$P_2 = 2I_0^2 J_2^2(\alpha) \cos^2\phi \quad (3)$$

Thus the sum of the powers in the first two harmonics $P_1+P_2$ is independent of $\phi$ only for those piezo amplitudes for which $j_1^2(\alpha) = J_2^2(\alpha)$. The lowest value of $\alpha$ for which this occurs is $\alpha=2.63$, leading to a piezo displacement $2\text{-}D_o$ of 0.419$\lambda$. At this particular modulation amplitude, the sum $P_1+P_2$ is independent of drifts in the pathlength difference between the two arms and is therefore a useful measure of the AC-coupled interferometer output fringe intensity.

Figure 9:
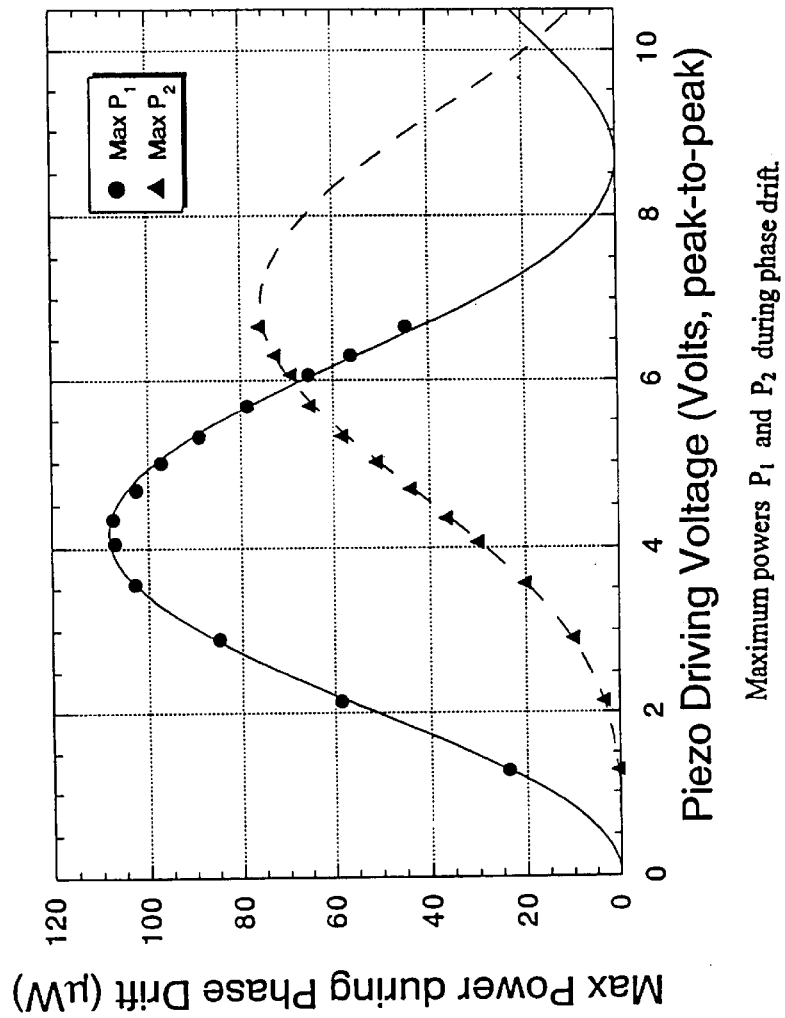
FIG. 9 shows the experimental values for the powers of the interferometer output signal in the first two harmonics as a function of the piezo driving voltage.

FIG. 9 shows the experimental values for the powers of the interferometer output signal in the first two harmonics as a function of the piezo driving voltage. For each setting of the driving voltage, the powers at 122 kHz and at 244 kHz were observed with a spectrum analyzer as they varied with the drifting phase, and their maximum values were plotted. The solid and dashed lines indicate the best fits to the equations $P_1 = k_1 J_1^2(r_1 x)$ and $P_2 = k_2 J_2^2(r_2 x)$, where $k_1$, $k_2$, $r_1$, and $r_2$ are fitting parameters. As expected, the fitted values of $k_1$ and $k_2$ were the same to within 1%, and the values of $r_1 x$ and $r_2 x$ at a piezo voltage of $x=5.95$ Volts peak-to-peak were within 1% of 2.63. At this point the sum of powers $P_1+P_2$ was observed to be independent of phase drift.

5. Discussion

A high fringe frequency has been achieved by driving a piezo at this same frequency and using a piezo resonance to obtain a modulation amplitude of roughly one fringe. It is also possible to achieve high fringe frequencies by driving a piezo at low frequencies but with large displacement amplitudes. By wrapping 100 m of fiber around a piezo tube, Cruz et al. reached fringe frequencies of 1 GHz with a peak-to-peak pathlength difference of 14 mm. In this case, phase drift ceases to be a problem because of the long train of fringes before the phase break associated with piezo reversal. However, the large interferometer path differences inherent in this approach are incompatible with the operation of the OCM of the invention.

The OCM of the invention collects three-dimensional images by performing a series of fast two-dimensional scans in planes normal to the incident beam and at regular depth intervals in the sample. These two-dimensional "en face" scans are performed at depths determined by the interferometer's equal path length position in the sample. Because the typical depth interval for the OCM is about 5 $\mu$m, modulation in the path length difference must be limited to about 1 $\mu$m during one of the en face scans. Larger modulations would degrade the depth resolution of the OCM. Hence a piezo stack driven at its resonance frequency has provided both a high fringe frequency for fast OCM image acquisition and a small modulation amplitude for good depth resolution.

6. Conclusion

A piezoelectric stack, when glued to an aluminum disk, displays a number of mechanical resonances between 50 and 350 kHz. The piezo is driven at its 125 kHz resonance for fast phase modulation in a Michelson interferometer. With a driving voltage amplitude of 6 V peak-to-peak, a piezo displacement of about 360 nm (0.42 $\lambda$) is achieved. The long-term performance of the piezo under these conditions is reliable; in particular, no heating or other damage to the stack has been observed. The measured rms value of the AC-coupled interferometer output experiences large variations due to phase wander between the reference and sample arms of the interferometer. However, for a piezo displacement of 0.42 $\lambda$, the sum of the powers of the first two harmonics of the driving frequency provides a measure of the interferometer output that is independent of phase drifts.

B. Modifications to the basic OCM design to enhance speed of image capture

Figure 10:
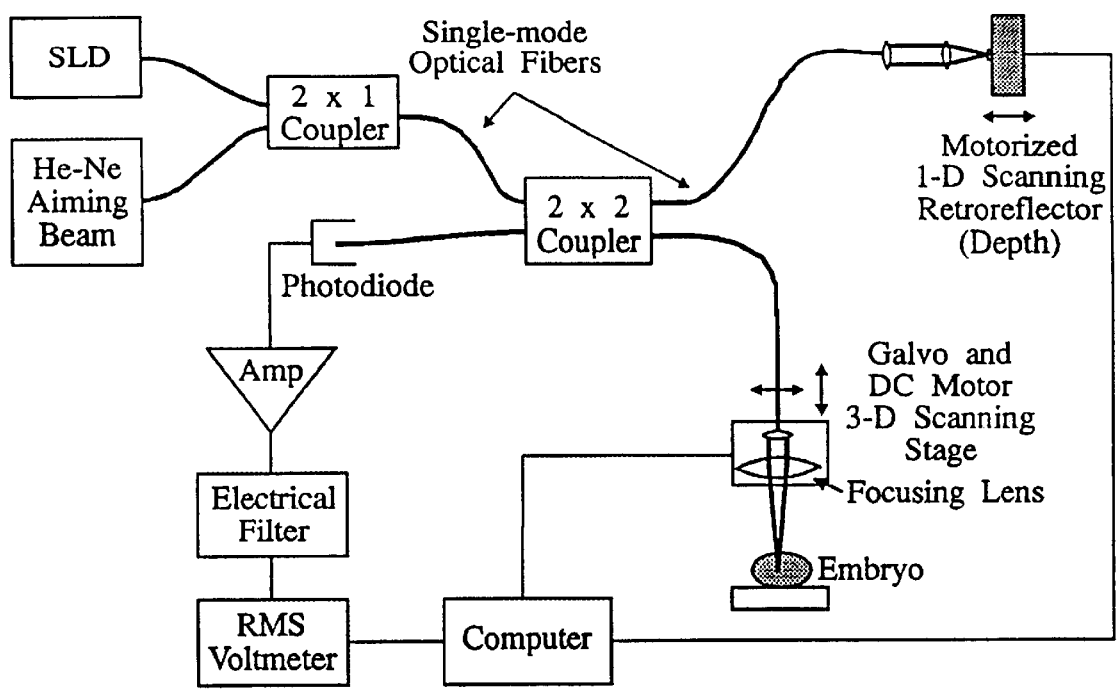
FIG. 10 is an optical schematic of a modified OCM.

A modified OCM was constructed that is capable of collecting a million-voxel image in less than a minute. An optical schematic of the instrument appears as FIG. 10. The key changes in design from the original OCM involve the introduction of galvo-scanning mirrors for the x-y scans and the use of a piezo-mounted mirror for the production of interferometer fringes.

1. Galvo-Scanning Mirrors

A pair of orthogonal galvoscanners (Model 6800-XY, Cambridge Technology Inc.) deflects the collimated beam emerging from the sample fiber and varies its angle of incidence upon the focusing lens, thereby scanning the focused waist of the beam across the x-y plane in the sample. The galvoscanners can be operated at up to 1 kHz. The beam spends about 20 microseconds on a voxel, so a linear scan along the x-axis of 100 voxels takes 2 milliseconds. The fast x-axis galvo is operated at slightly less than 500 Hz. A million-voxel image could therefore be taken in 20 seconds, though overhead in processing each x-y scan and moving the DC motor actuators along the z-axis increases the collection time to 40 to 60 seconds. The galvoscanners were calibrated by imaging a Ronchi ruling with a period of 20 μm.

2. Generating Fast Interferometer Fringe

The brightness of a voxel in an OCM image is proportional to the amplitude of the OCM interferometer fringes. At each voxel, the amplitude of the fringes must be determined. The modified OCM spends just 20 microseconds on a voxel, so the frequency of the fringes must be at least 50 kHz. To achieve this frequency, a small reference mirror (1.5 mm×1.5 mm×0.1 mm, Edmund Scientific Co.) was glued to a piezoelectric stack (AE0203-DO4, Thorlabs) with a resonant frequency of 250 kHz. When the mirror and stack were epoxied to an aluminum disk (diameter=25 mm, thickness=5 mm), the resonant frequency split into a number of resonances, a strong one being at 120 kHz. At this resonance, a driving voltage of 6 volts peak-to-peak is sufficient to displace the mirror by 0.42×850 nm=357 nm (peak-to-peak). This modification is reviewed in more detail in Example IA, above.

The mirror/piezoelectric stack forms the rear end of the retroreflector in the reference arm of the OCM interferometer. As the mirror is oscillated piezoelectrically at 120 kHz, the path length difference in the interferometer varies and 120 kHz fringes appear at the output. The fringes are isolated with a narrow bandwidth electrical filter, and the output is then sent to an rms circuit. A commercially available integrated circuit is the AD63 7 (Analog Devices) that measures the amplitude of the fringes to better than 10% in approximately two periods of the fringe signal. Two periods at 120 kHz amount to 17 microseconds, so the beam spends 20 microseconds on each voxel.

3. Elimination of interferometer phase noise

Like all Michelson interferometers, the path length difference between the sample and reference arms of the OCM drifts slowly by roughly a half-wavelength (one fringe) due to air currents, temperature effects, etc. This phase drift causes the fringe signal to shift power from the fundamental piezoelectric driving frequency (120 kHz) to higher harmonics and to a DC offset. As a result, the output of the rms circuit may vary by 30 to 50% even when the scattering power of the voxel remains constant. This problem is solved by constructing the electrical filter to pass the fundamental and first harmonic frequencies. In addition, using a sinusoidal driving voltage for the piezo stack, the amplitude of motion of the reference mirror is adjusted to 0.42×850 nm=357 nm (peak-to-peak). At this amplitude the output of the rms circuit is independent of the phase drift in the OCM interferometer. This is a useful result for reducing noise in an OCM image.

4. Elimination of birefringence drift

The design of the modified OCM has another notable advantage over that of the original OCM. In the original OCM, about 10 m of optical fiber was wrapped under tension around a piezoelectric cylinder. A driving voltage was applied to the cylinder, stretching and contracting the fiber, and causing the optical path length of the fiber to oscillate. A fiber/cylinder system was inserted into each of the sample and reference arms of the OCM interferometer. These two piezoelectric cylinders were driven 180° out of phase to produce fringes at the output of the OCM interferometer. The stretching of these long lengths of fiber led to noticeable stress birefringence, and "paddles" were incorporated to twist the fiber systematically until the optical path lengths for the two polarization states of the beam were equal. The setting of the paddles was subject to drift, leading to distorted visibility curves of the interferometer fringes.

In the modified OCM, the lengths of the optical fiber in the sample and reference arms are just 1 meter. No stretching of the fiber occurs, and no distortion of the Gaussian visibility curve over time has been noted.

Example II

Software for Viewing 3-D OCM Images

Three-dimensional OCM images can be generated by adapting available visualization software, such as, for example, AVS (Advanced Visual Systems) Version 5.0 to display 3-D OCM images on Unix workstations. For greater convenience VISUALIZATION EXPRESS, also by AVS does not require a Unix workstation. VISUALIZATION EXPRESS is written in OpenGL, which allows graphics applications to be ported to many software/hardware platforms. This software was adapted to create a custom graphical user interface called "Intuitive Network" within Visualization Express and achieved increased flexibility and power. The following is a brief description of the fundamental principles of this image-display software package.

Principles of Volume-Rendering

During image acquisition, the OCM assigns a single number to each of the roughly one million voxels scanned in the sample volume. To first approximation, this number is a measure of the light scattering power of the associated voxel. To visualize one of these 3-D data volumes, all voxels must be projected onto a 2-D computer screen for viewing. The process of projecting voxels, including assigning the relative weights of voxels deep within the volume versus near the surface of the volume, is called volume rendering.

The basic algorithm for volume rendering is ray tracing. Every pixel in the 2-D image to be generated on the computer screen determines a ray that is drawn from the pixel on the 2-D screen through the 3-D data volume. A "parallel projection" is employed, in which projected rays are parallel to each other. All voxels in the volume along a ray contribute to the value of the corresponding pixel on the 2-D computer screen. Because a ray does not always go through the centers of voxels that it intersects, there are different ways to compute (or "blend") the contributions of voxels along the ray. For example, one may consider all voxels in the vicinity of the ray and calculate the sum of their voxel contents weighted inversely by their distances to the ray. Alternatively, for simplicity and therefore reduced computational cost, one may use only those voxels penetrated by the ray and sum their voxel contents (unweighted).

Another feature involved in the blending of voxels along a ray is the "opacity" factor. The content of each voxel is multiplied by the opacity factor as the sum is formed along a given ray. If the opacity factor for all voxels is zero, no voxel contributes to a pixel, and the pixel is black. If the opacity factor for all voxels is one, the voxel contents are summed along the ray and the resulting pixel may contain a large number, perhaps a number representing saturation. Small values for the opacity factor tend to avoid saturation and allow voxels deep in the image volume to contribute meaningfully to the corresponding pixel. That is, small values of the opacity factor tend to impart a more "transparent" appearance to the image volume.

Use of False Color

The OCM of the invention assigns a raw number (grey level) to a voxel based upon its measured light scattering power. AVS VISUALIZATION EXPRESS uses false color to help distinguish different grey levels in the raw voxel contents. Two different ways were used for implementing false color in the volume-rendering algorithms available in AVS Express. The simpler way, named "SFP", is to apply the ray-tracing algorithm for volume rendering (described above) to the raw greyscale contents of voxels. The resulting 2-D greyscale pixels are then color coded, e.g., weak pixels are assigned the color blue and strong pixels are colored red. However, in this method a particular region of the 3-D volume may change color drastically as the volume is viewed from different vantage points. For example, two green voxels can be superposed along a particular line of sight to yield a red pixel.

More preferred is a second method of implementing false color in AVS Express. In the volume-rendering method named "DC", the raw contents of voxels are color coded, i.e., values for red, green, and blue are assigned to each voxel based upon the voxel's raw grey level. Then the ray tracing algorithm for volume rendering is executed separately for all three colors to generate a colored 2-D image on the computer screen. This DC method does indeed superpose two green voxels to yield a strong green pixel. In this way, a region of the image volume with a particular light-scattering strength will retain its color, at least approximately, as the volume is rotated on the screen.

The software allows anatomical, morphological and histological aspects of plants, frogs, and other organisms to be examined. Examples of AVS software settings are as follows:

Ray Tracing Algorithm: Direct Composite
Interpolation: trilinear
Control Points
   Control Point 1 position: 2
   Control Point 2 position 23
Range 1 settings:
   Transparency Left=1.0
      Hue=0
      Saturation=0
      Value=0
   Transparency Right=1.0
      Hue=0.66
      Saturation=1.0
      Value=1.0
Range 2 settings:
   Transparency Left=0.91
      Hue=0.66
      Saturation=1.0
      Value=1.0
   Transparency Right=0.95
      Hue=0
      Saturation=1.0
      Value=1.0
Range 3 settings:
   Transparency Left=0.69
      Hue=0
      Saturation=1.0
      Value=1.0
   Transparency Right=1.0
      Hue=0
      Saturation=1.0
      Value=1.0

Example III

Developmental biology of the plant *Arabidopsis thaliana*

A. To study meristem formation in the developing embryo, plants were grown in four-inch pots in soil in a growth chamber under 16-hour day lengths, to accelerate the transition to reproductive growth. During flower formation, Arabidopsis internodes elongate extensively. Thus a single silique, with its developing embryos inside, was easily placed between two glass microscope slides without disturbing the rest of the plant or removing the silique from the plant. The silique was mounted shortly after fertilization to follow the development of the embryos over the course of the few days (from a globular embryo to a fully expanded embryo). The OCM images allowed precise observation of development of a single embryo over time. The pattern of development in wild-type embryos was compared with those of mutant embryos to gain better insights into the altered embryogenic patterns.

B. The OCM was also used to study the temporal changes in the shoot apical meristem and shoot apex during successive leaf initiations. For these observations, the plants were grown in four-inch pots in soil under an 8-hour day length to inhibit the transition from vegetative to reproductive development. These growth conditions permitted observation of meristem activity over many consecutive leaf initiation events. As humidity variations appeared to have significant effects on plant growth rates, it is preferable to maintain the plants in a humidity-controlled growth chamber. In addition to allowing precise regulation of the environment in which the plants grow, such a chamber allows growth of populations of plants under long-day conditions (for studies on embryo formation) and short day conditions (for studies on phyllotaxy) at the same time.

In this procedure, the volume and shape of the shoot apical meristem and shoot apex over the course of several days was observed. The meristem and shoot apex were examined from above to ensure that each leaf, no matter where it initiated, was imaged with equal fidelity. By this approach, insights are gained into the changes in the shoot apex and shoot apical meristem as it undergoes developmental changes, such as forming successive leaves, and the processes of mutants may be characterized in comparison to wild-type plants.

C. Studies of Plant Images. An image of a plant shoot (*Arabidopsis thaliana*) was obtained using the OCM of the invention. The volume of the image is 600$\mu$m×600$\mu$m×400 $\mu$m (width×width×depth) with a voxel size of $(10\ \mu m)^3$. In a top view straight down along the beam and along the shoot axis, the petioles of the cotyledons and leaves 1 and 2 were visible growing out from the center of the plant shoot. The shoot apical meristem was evident when the image was cropped as a highly scattering region at the base of the leaves. The gl-l (glabrous) mutant of *Arabidopsis thaliana* was used to avoid high light scatter from trichomes.

A rotated image of the leaf and meristem region was visualized, having a volume of (200 $\mu$m×200 $\mu$m×120 $\mu$m) (width×width×depth) with a voxel size of $(2\ \mu m)^3$. As a side view, with the beam incident from the top of the figure, the leaves were seen growing out from the center of the shoot. The meristem and shoot apex were evident at the base of the leaves.

Several images in a series were taken for each of ten Arabidopsis seedlings during days 5 through 12 of development when leaf primordia were formed and a spiral pattern of leaves emerged. In these images it was possible to identify the shoot apical meristem and/or associated leaf primordia, supporting the conclusion that OCM can follow non-invasively the morphological development of a single plant. The images may indicate that the regions of highest light scattering correspond to areas of highest cellular activity. Leaf primordia and the presumed shoot apical meristem scatter highly, and are sites of rapid cell division. Accordingly, high cellular activity may serve as an intrinsic probe for OCM.

In an OCM image of a 5-day-old Arabidopsis plant, the "opacity" parameter (see Example III on the image-rendering software) was adjusted so that opacity was high. With this setting, weakly scattering tissues (blue) surrounding strongly scattering tissues (red/yellow) hid the strongly scattering regions from view. The overall effect was that the "outside" of the plant was visible, as in a scanning electron micrograph. By cropping or slicing into the image plane of the strongly scattering tissue, the red/yellow was exposed.

In another OCM image of the same 5-day-old plant, the opacity parameter was adjusted low so that voxels deep in the tissue could be seen. Using these procedures, it was possible to unambiguously identify many of the larger (>30 $\mu$m) organs at the shoot apex. Identifying the smaller leaf primordia was more difficult. To unambiguously identify the smaller organs, frequent observations were made, e.g., every hour or two, to observe their increase in size during development. All images were acquired with the original OCM which requires 3 hours for a million-voxel image. Therefore a single image averages over significant growth, and this averaging is probably a factor in the resolution of the image. The modified OCM has an image acquisition time of 5 minutes or less for similar images. Use of the modified OCM produced a series of images more closely spaced in time, and allowed identification of leaf primordia as they emerged from the meristem.

In a side-by-side comparison of an OCM image of a living plant with a histological section of a different plant, the OCM image included leaves and a small, strongly scattering region that was consistent with a leaf primordium. The histological section of a comparable plant supported this interpretation. The OCM image was cropped from the top and was an "outside" image (high opacity), so that the meristem below was not visible. In following the development of an individual plant, it is helpful to detect an emerging leaf primordium as early as possible. While the resolution of the histological slide was clearly superior, only the OCM images were able to follow the subsequent development of the emerging leaf primordium.

In direct comparison of OCM and traditional sections, plants were imaged with OCM and fixed for traditional analysis. The OCM image showed leaf primordia and cotyledon petioles. The amount of light scatter was proportional to the color. A simple spectrum was set up such that red was the highest amount of light scatter, orange-yellow was less, green less, blue-black least. Cells and tissues that were active (e.g., transcription and differentiation) produced the greatest amount of light scatter.

In optical sections and traditional plastic sections deeper in a plant, an OCM image of deeply buried tissue was visualized. The leaf primordia were seen and a recently formed stipule was also seen. Stipules, which are known to be very active transcriptionally, produced a large amount of backscattered light in OCM, and hence appeared as red on the OCM image.

In OCM and traditional section of developing organs and the apical meristem, one leaf primordium was seen as just adopting a dorsoventral symmetry whereas a less mature leaf primordium was seen as not being dorsoventral, still retaining centric features. Thus, OCM can detect these differences. The more advanced leaf primordium appeared as a red, rectangular-shape and the less advanced leaf primordium appeared as a red, round-shape. The meristem, detectable in a plastic section in a different focal plane also appeared as a red rectangular shaped object. Thus, OCM can follow and predict developmental changes taking place deep within tissues in vivo in a non-destructive manner.

A comparison was conducted of OCM and scanning electron micrography of an Arabidopsis mutant, shootmeristemless. The shootmeristemless mutant is known to lack a shoot apical meristem (Barton and Poethig, 1993). In wild-type plants, the apical meristem appeared as a red, highly light scattering structure. As predicted, in the shootmeristemless mutant there was no such structure. Instead a gap indicating a lack of a shoot apical meristem was detected.

Thus, the OCM can be used, not only to visualize structures in a biological sample, but also to visualize developmental stages, processes, and events, to contrast mutants with non-mutants or to grade mutant or allelic series, and the like. The effect of a variety of factors on light scattering can also be used to characterize biological samples with respect to such factors, including, for example, gene activity, differentiation, cell elongation, cell dormancy, stress response, pathogen response, and the like. Uses of light scattering comparisons employing the OCM of the invention will be evident to those engaged in such comparisons, for correlating light scattering or other OCM image characteristics with a variety of conditions, structures, and events of interest.

Example IV

Developmental Biology of the Frog *Xenopus laevis*

A. Xenopus embryos are mounted in a small, triangular well cut in a layer in the bottom of a petri dish coated with silicone rubber. A 100 $\mu$m thick sheet of gelled agarose is placed over the top of the embryo and secured in place with thin cactus spines stuck into the silicone rubber. This method of stabilizing the embryo keeps the embryo in a defined position and orientation, without the danger of distorting the cell movements under study. During gastrulation, a set of three-dimensional images through the thickness of the animal pole of the embryo is collected. These three-dimensional data sets are processed and rendered into a time-lapse movie. As the resolution of the OCM is smaller than the single cells, these images are adequate to follow the tissue movements of gastrulation. Alternatively, two-dimensional images may be collected, in the plane bisecting the embryo along its midline. This offers rapid frame rates, and therefore better details on the cell movements within this reduced field of view.

B. Additionally, the OCM system is used to examine the morphological patterning of the mesoderm after it involutes. This process is critical for the resulting structures, such as the notochord and the somites, as well as for the nervous system. Interactions between the notochord and the spinal cord affect the dorsoventral patterning of the nervous system, and interactions with the somites result in segmentation of the sensory nervous system and the ventral roots of the motoneuron axons formed by the spinal cord. The experimental arrangement described above is used to stabilize the embryos, and the OCM is employed to collect images needed for 2- and 3-dimensional time-lapse movies.

C. Studies of Frog Embryo Images. An image was taken of a frog embryo that was lightly fixed (2% paraformaldehyde overnight at 4° C. in stage 41 of development). The head region that was imaged was (1.6 mm×1.6 mm×1.3 mm) (width×width×depth). The voxel size was (20 $\mu$m)$^3$. In the figure the embryo (tadpole) was on its right side and was viewed along a body axis from tail to head, so that the ventral-dorsal axis pointed left to right. The beam was incident from the top of the image. The bulge of the left eye was clearly evident at the top of the image. Red and yellow areas denoted highly scattering regions, and blue and black denoted more transparent regions.

Another image of the same frog embryo was taken, but at slightly higher magnification. The volume imaged was (600 $\mu$m×600 $\mu$m×420 $\mu$m) (width×width×depth), and the voxel size was (6 $\mu$m)$^3$. The beam was still incident upon the embryo's left side from the top of the image. The view was again along the body axis, but looking toward the tail, so the dorsal side was on the left and the ventral side was on the right. The 600 $\mu$m long segment that was imaged was further down the body from the head. The 420 $\mu$m depth was oriented top-bottom in the figure, and the 600 $\mu$m dorsal-ventral width lay left-right. The 3-D image was been carefully rotated so that the view was straight down the axis of the spinal cord a rotation of just one degree about the beam axis (top-bottom axis) would obscure the structure that was obvious at the selected viewing angle.

What is claimed is:

1. A high resolution optical coherence microscope system for visualizing structures below a surface of a biological sample, the system comprising:
   a light source emitting light in a wavelength of between 700 and 1500 nm;
   a reference mirror;
   a focusing lens for focusing light on the biological sample;
   a photodetector;
   a sample optical path for receiving light from the light source and directing the light to the focusing lens, said sample path having a sample path length, wherein the light directed along the sample path enters the biological sample and tapers to a beam waist diameter within the sample;
   a reference optical path for receiving light from the light source and directing the light to the reference mirror, said reference path having a reference path length;
   a piezoelectric device, wherein the length of at least one of the optical paths is modulated by the piezoelectric device, and wherein a light beam from the sample optical path scattered back from the biological sample is combined with a light beam from the reference path reflected from the reference mirror, wherein the combination of light beams produces an interference fringe signal on the photodetector when the sample path length and the reference path length are substantially the same to within the coherence length of the light source, wherein an amplitude of modulation is less than 0.50 of the wavelength, and the powers in a fringe signal at a fundamental frequency, f, and a second harmonic of the fundamental frequency, 2f, are summed to provide a measure of the amplitude of the fringes; and
   a scanner arranged to scan the beam waist across a first plane substantially normal to the direction of the incident light beam, and to then move the beam waist deeper into the sample and to scan another plane while the position of the reference mirror is translated to keep the equal path lengths of the sample and reference paths coincident with the beam waist, and that the fringe amplitude is recorded at each volume element voxel during the scan of the sample resulting in a three-dimensional data set that is volume-rendered to provide a three-dimensional visualization of the sample.

2. The system of claim 1, wherein the modulation occurs at a frequency of at least about 50 kHz.

3. The system of claim 1, wherein the modulation occurs at a frequency of at least about 100 kHz.

4. The system of claim 1, wherein the modulation occurs at a frequency of at least about 300 kHz.

5. The system of claim 1, wherein the light directed along the sample path scans the biological sample, and wherein the scan results in an image of a portion of the biological sample, wherein the portion is between about 100 $\mu$m and about 4000 $\mu$m below the surface of the sample.

6. The system of claim 5, wherein the image comprises a first layer, the first layer derived from a first plurality of voxels all corresponding to substantially a same first depth below the surface of the sample.

7. The system of claim 6, wherein the image further comprises a second layer, the second layer derived from a second plurality of voxels all corresponding to substantially a same second depth below the surface of the sample.

8. The system of claim 7, wherein the image comprises at least about 50 distinct layers, including said first and second layers, wherein each of the layers is derived from a distinct plurality of voxels, and wherein all voxels for each distinct layer correspond to substantially a same distinct depth below the surface of the sample.

9. The system of claim 7, wherein the image comprises blended voxels of a plurality of layers including said first and second layers, and wherein the image is a three-dimensional rendering of the portion of the biological sample.

10. The system of claim 1, further comprising a coherence volume about a plane at which the length of the sample is equal to the length of the reference path, wherein the coherence volume exists below the surface of the biological sample.

11. The system of claim 10, wherein the light from the sample path enters the sample and tapers to said beam waist diameter, wherein the beam waist diameter is not more than 20 $\mu$m within the sample, and wherein the beam waist is coincident with the coherence volume, such that lateral resolution of structures within the sample is a distance less than or equal to the diameter of the beam waist.

12. The optical coherence microscope system of claim 1, wherein the light beam directed along the sample path scans the biological sample, and wherein the scan results in an image of a portion of the biological sample, wherein the portion is between about 100 micrometers and about 4000 micrometers below the surface of the sample.

13. The optical coherence microscope system of claim 1, wherein the amplitude of modulation is equal to about 0.42 of the wavelength.

14. The optical coherence microscope system of claim 1, wherein the coherence length of the light source determines the depth resolution of the microscope system.

15. The optical coherence microscope system of claim 1, wherein the piezoelectric device is a piezoelectric stack having the reference mirror mounted thereon.

16. A method of visualizing a structure beneath a surface of a biological sample comprising the steps of:
   providing light having a wavelength between 700 and 1500 nm;
   dividing the light into a sample light path and a reference light path;
   modulating the length of at least one of the light paths with a piezoelectric device, wherein the modulation of the path length occurs at a frequency, f, of at least 50 kHz and amplitude of modulation is less than 0.50 of the wavelength;

directing light from the sample path into the biological sample with a focusing lens, wherein the light enters the biological sample and tapers to a beam waist within the sample, scanning the beam waist across a first plane substantially normal to the direction of the incident light beam;

combining a light beam from the sample light path scattered back from the biological sample with a light beam from the reference light path reflected by a reference mirror, wherein the combination of light beams produces an interference fringe signal on a photodetector when the sample light path length and the reference light path length are substantially the same to within the coherence length of the light source;

moving the beam waist to a different depth within the sample and scanning another plane while the position of the reference mirror is translated to keep the equal path lengths of the sample and reference light paths coincident with the beam waist;

summing the powers in the fringe signal at a fundamental frequency, f, and a second harmonic of the fundamental frequency, 2f, to provide a measure of the amplitude of the fringes; and recording the fringe amplitude at each volume element, voxel, during the scan of the sample resulting in a three-dimensional data set that is volume-rendered to provide a three-dimensional visualization of the sample.

17. The method of claim 16, wherein the directing step is repeated at least 100 times, and wherein after each directing step, the method comprises the additional step of translocating the sample light path to a different position in the biological sample.

18. The method of claim 16, wherein the image indicates a difference between a mutant biological sample and a non-mutant biological sample.

19. The method of claim 16, wherein the image comprises a pattern of light scatter, and wherein the pattern correlates with a characteristic of the biological sample.

20. The method of claim 19, wherein the characteristic is selected from the group consisting of gene activity, differentiation, cell elongation, cell dormancy, stress response, and pathogen response.

21. The method of claim 16, wherein the amplitude of modulation is equal to 0.42 of the wavelength.

22. A high resolution optical coherence microscope system for visualizing structures below a surface of a biological sample, the system comprising:

a light source emitting light in a wavelength of between 700 and 1500 nm;

a reference mirror:

a focusing lens for focusing light on the biological sample;

a photodetector;

a sample optical path for receiving light from the light source and directing the light to the focusing lens, said sample path having a sample path length, wherein the light directed along the sample path enters the biological sample and tapers to a beam waist diameter within the sample;

a reference optical path for receiving light from the light source and directing the light to the reference mirror, said reference path having a reference path length a piezoelectric device, wherein the length of at least one of the optical paths is modulated by the piezoelectric device, and wherein a light beam from the sample optical path scattered back from the biological sample is combined with a light beam from the reference path reflected from the reference mirror, wherein the combination of light beams produces an interference fringe signal on the photodetector when the sample path length and the reference path length are substantially the same to within the coherence length of the light source, wherein an amplitude of modulation is equal to or less than 1.0 of the wavelength, and the powers in a fringe signal at two adjacent harmonic frequencies of the fundamental frequency, f, are summed to provide a measure of the amplitude of the fringes.

a scanner ranged to scan the beam waist across a first plane substantially normal to the direction of the incident light beam, and to then move the beam waist deeper into the sample and to scan another plane while the position of the reference mirror is translated to keep the equal path lengths of the sample and reference paths coincident with the beam waist, and that the fringe amplitude is recorded at each volume element, voxel, during the scan of the sample resulting in a three-dimensional data set that is volume-rendered to provide a three-dimensional visualization of the sample.

23. The system of claim 22, wherein the two adjacent harmonic frequencies are the first harmonic fundamental frequency, f, and the second harmonic fundamental frequency, 2f.

* * * * *